US006710033B1

(12) United States Patent
Stratton et al.

(10) Patent No.: US 6,710,033 B1
(45) Date of Patent: Mar. 23, 2004

(54) METHODS AND TREATMENT OF MULTIPLE SCLEROSIS

(75) Inventors: Charles W. Stratton, Nashville, TN (US); William M. Mitchell, Nashville, TN (US); Subramaniam Sriram, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/528,348

(22) Filed: Mar. 17, 2000

Related U.S. Application Data

(63) Continuation-in-part of application No. 09/073,661, filed on May 6, 1998, which is a continuation-in-part of application No. 09/025,174, filed on Feb. 18, 1998, which is a continuation-in-part of application No. 08/911,593, filed on Aug. 14, 1997.
(60) Provisional application No. 60/023,921, filed on Aug. 14, 1996, provisional application No. 60/125,598, filed on Mar. 19, 1999, provisional application No. 60/176,662, filed on Jan. 18, 2000, provisional application No. 60/176,940, filed on Jan. 18, 2000, and provisional application No. 60/176,784, filed on Jan. 18, 2000.

(51) Int. Cl.[7] .................. A61K 31/70; A61K 31/47; A61K 31/415
(52) U.S. Cl. .................. 514/29; 514/31; 514/311; 514/312; 514/313; 514/314; 514/398; 514/903
(58) Field of Search .................. 514/29, 31, 311, 514/312, 313, 314, 398, 903

(56) References Cited

U.S. PATENT DOCUMENTS

| 3,996,355 | A |   | 12/1976 | Lin et al. ................. 514/86 |
| 4,952,594 | A | * | 8/1990  | Mercer .................. 514/398 |
| 5,217,493 | A |   | 6/1993  | Raad et al. .............. 623/11.11 |
| 5,650,405 | A |   | 7/1997  | Remington et al. ........ 514/183 |
| 5,795,563 | A |   | 8/1998  | Kallick .................. 424/9.361 |
| 5,834,485 | A | * | 11/1998 | Dyke et al. ............. 514/311 |
| 5,869,608 | A |   | 2/1999  | Caldwell et al. ......... 530/350 |
| 5,880,101 | A | * | 3/1999  | Stankov ................. 514/29 |
| 6,043,225 | A |   | 3/2000  | Shor et al. ............. 514/29 |
| 6,043,227 | A |   | 3/2000  | Cheng et al. ........... 514/29 |
| 6,057,367 | A |   | 5/2000  | Stamler et al. ......... 514/561 |

FOREIGN PATENT DOCUMENTS

| CN | 1 156 589   | 8/1997 |
| CN | 1 190 581   | 8/1998 |
| EP | 0439330     | 1/1991 |
| EP | 0699688     | 3/1996 |
| FR | 2134292     | 8/1992 |
| WO | WO 90/00061 | 1/1990 |
| WO | WO 98/06408 | 2/1998 |
| WO | WO 98/06435 | 2/1998 |
| WO | WO 98/10789 | 3/1998 |
| WO | WO 98/17280 | 4/1998 |
| WO | WO 98/24362 | 6/1998 |
| WO | WO 98/47509 | 10/1998 |
| WO | WO 98/50074 | 11/1998 |
| WO | WO 98/51696 | 11/1998 |
| WO | WO 98/58953 | 12/1998 |
| WO | WO 99/17741 | 4/1999 |
| WO | WO 99/21865 | 5/1999 |
| WO | WO 99/21866 | 5/1999 |
| WO | WO 00/01378 | 1/2000 |

OTHER PUBLICATIONS

Appelt et al., "Is there an association of β–Amyloid with *Chlamydia pneumoniae* in glial and monocyte cell lines infected with the bacterial with the bacterial isolates obtained from alzheimer disease brains?" *Society for Neuroscience Abstracts* 25:42 (1999).

Balin et al., "Identification and localization of *Chlamydia pneumoniae* in the Alzheimer's brain," *Society for Neuroscience Abstract* 24:1957 (1998).

Balin et al., "Identification and localization of *Chlamydia pneumoniae* in the Alzheimer's Brain," *Medical Microbiology and Immunology* 187:23–42 (1998).

Bertrand et al., "L'ofloxacine (Ru 43280) étude clinique" *Path Biol.* 35: 629–633 (1987).

Brocke et al., "Induction of releasing paralysis in experimental autoimmune encephalomyelities by bacterial superantigen," *Nature* 365:642–644 (1993).

Drancourt et al., "Oral rifampin ofloxacin for treatment of staphylococcus –infected orthopedic implants" *Antimicrobial Agents and Chemotherapy* 37:1214–1218 (1993).

Freidank et al., "In vitro susceptibilities of *Chlamydia pneumoniae* isolates from german patients and synergistic activity of antibiotic combinations" *Antimicrobial Agents and Chemotherapy* 43:1808–1810 (1999).

Gieffers et al., "Failure to detect *Chlamydia pneumoniae* in brain sections of Alzheimer's disease patients," *Journal of Clinical Microbiology* 38:881–882 (2000).

Jahnke et al., "Sequence homology between certain viral proteins and proteins related to encephalomyelitis and neuritis," *Science* 229:282–284 (1985).

Korman et al., "Neurological complications of chlamydial infections: case report and review," *Clinical Infectious Disease* 25:847–851 (1997).

Kurtzke, "Epidemiologic evidence for multiple sclerosis as an infection," *Clinical Microbiology Reviews* 6:382–427 (1993).

(List continued on next page.)

Primary Examiner—Kevin E. Weddington
(74) Attorney, Agent, or Firm—Clark & Elbing LLP

(57) ABSTRACT

The invention features methods and reagents for the diagnosis, monitoring, and treatment of multiple sclerosis. The invention is based in part on the discovery that Chlamydia is present in patients with multiple sclerosis, and that anti-chlamydial agents improve or sustain neurological function in these patients.

18 Claims, 16 Drawing Sheets

OTHER PUBLICATIONS

Layh–Schmitt et al., "Evidence for Infection with *Chlamydia pneumoniae* in a subgroup of patients with multiple sclerosis" *Annals of Neurology* 47:652–655 (2000).

Le Gac et al., "Sur une etiologie rickettsienne et neo–rickettsienne possible de la sclerose en plaques," *Comptes rendus* 250:1937–1938, (1960).

LeGac, "Le traitement de la sclerose en plaques d'origine rickettsienne ou neo–rickettsienne," *Comptes rendus* 250:2474–2476, (1960).

LeGac, "Le probleme histo–physio–patho–logique de la sclerose en plaques," *Comptes rendus* 250:2299–2303, (1960).

LeGac et al, "Le virus de la psittacose dans l'etiologie de la sclerose en plaques," *Comptes rendus* 263:1793–1797, (1966).

LeGac, "Rickettsioses, pararickettsioses et systeme nerveux," *Ann.. Ist. Super. Sanita* 10:275–296 (1974).

LeGac et al., "Resultats de L'antibiotherapie large spectre sur 30 cas chroniques de sclerose en plaques rickettsienne et neo–rickettsienne," *Bulletin de la Societe de Pathologie Exotique* 2:263–276, (1964).

McHatters et al., "Bird virusses in multiple sclerosis: combination of viruses or Marek's alone?" *Neuroscience Letters* 188:75–76 (1995).

Nochlin et al., "Failure to detect *Chlamydia pneumoniae* in brain tissues of Alzheimer's disease," *Neurology* 53:1888 (1999).

Oldstone, "Virus–induced autoimmunity: molecular mimicry as a route to autoimmune disease," *Journal of Autoimmunity* 2(S):187–194 (1989).

Perlmutter et al., "Possible relationship of chlamydia to multiple sclerosis" *Medical Hypothesis* 12:95–98 (1983).

Renvoize et al., "A sero–epidemiological study of conventional infectious agents in Alzheimer's disease," *Age and Ageing* 16:311–314 (1987).

Rosenkranz, "Rifampicin and multiple sclerosis," *The Lancet* 2:1370 (1972).

Sever et al., "Virus antibodies and multiple sclerosis," *Achives Neurology* 24:489–494 (1971).

Sriram et al., "Multiple sclerosis associated with *Chlamydia pneumonia* infection of the CNS" *Neurology* 50:571–572 (1998).

Sriram et al., "*C. pneumonia* infection of the CNS in patients with relapsing remitting MS" *Neurology* 52:A558–A559 (1999).

Sriram et al., "*Chlamydia pneumoniae* infection of the central nervous system in multiple sclerosis" *Annals of Neurology* 46:6–14 (1999).

Sriram et al., "Indictment of the microglia as the villian in multiple sclerosis," *Neurology* 48:464–470 (1997).

Yao et al., "Association between *C. pneumoniae* and MS" *Journal of Neuroimmunology* 90:70 (1998).

Yao et al., "CNS infection with *C. pneumoniae* in MS," *Neurology* 50:A423–A424 (1998).

Yao et al., "Reactivity of oligoclonal bands seen in CSF to *C. pneumoniae* antigens in patients with multiple sclerosis," Neurology 52:A559 (1999).

\* cited by examiner

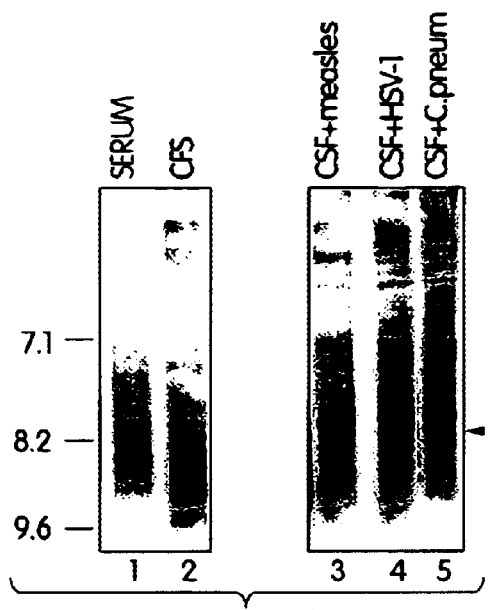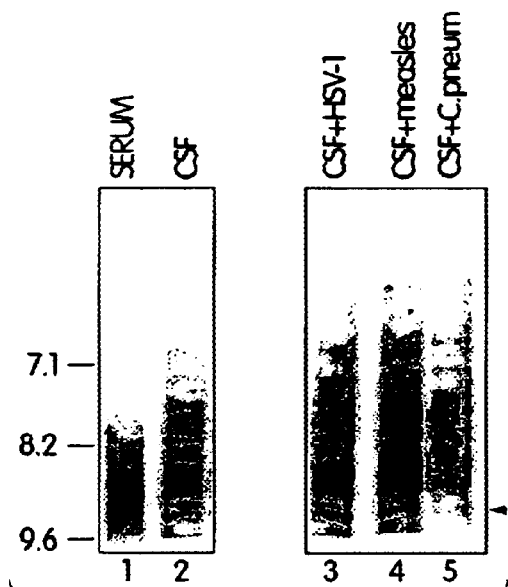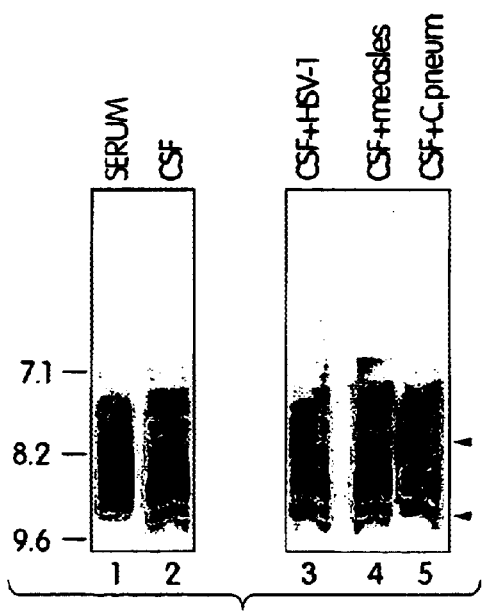
Fig. 6A
Fig. 6B
Fig. 6C

METHODS AND TREATMENT OF MULTIPLE SCLEROSIS

CROSS REFERENCE TO RELATED APPLICATIONS

This application is a continuation-in-part of U.S. application Ser. No. 09/073,661, filed May 6, 1998, which is a continuation-in-part of U.S. application Ser. No. 09/025,174, filed Feb. 18, 1998, which is a continuation-in-part of U.S. application Ser. No. 08/911,593, filed Aug. 14, 1997, which claims benefit of the filing date of U.S. Provisional No. 60/023,921, filed Aug. 14, 1996. This application also claims benefit of the filing dates of U.S. Provisional Application No. 60/125,598, filed Mar. 19, 1999, and U.S. Provisional Application Nos. 60/176,662, 60/176,940, and 60/176,784, each filed Jan. 18, 2000.

BACKGROUND OF THE INVENTION

Multiple Sclerosis (MS) is a chronic inflammatory disease of the central nervous system (CNS) in which the predominant pathologic findings are demyelination accompanied by disruption of underlying axons (Trapp et al., New Engl. J. Med. 338:278–285, 1998; Prineas, J. W., "Pathology of Multiple Sclerosis" in: Cook SD, ed. Handbook of Multiple Sclerosis. New York: Marcel Dekker, Inc, 1990:187–215). The disease affects young adults who usually present with a relapsing, remitting pattern of neurologic involvement and progress to a chronic phase with increasing difficulty in ambulation and coordination. The etiology of MS is not known, but there is considerable indirect evidence that argues for the role of an infectious agent(s) in the pathogenesis of the disease. Epidemiological studies strongly suggest that a CNS infection in early childhood is a key factor in the development of MS (Kurtzke, Clin. Microbiol. Rev. 6:382–427, 1993). Viral infections have long been thought to play a possible role in the pathogenesis of MS because viruses are known to cause demyelinating disease in experimental animals, often present clinically with relapsing, remitting symptoms, and can cause disease with long periods of latency (Cook and Dowling, Neurology 30:80–91, 1980; Johnson, R. T., Viral infections of the Nervous System. New York: Raven Press, 1982). Studies to date, however, have failed to identify any virus as playing a major role in MS, although activated human herpes virus 6 (HHV-6) has been identified recently in brains of MS patients (Sanders et al., J. Neurovirol. 2:249–258, 1996; Challoner et al., Proc. Natl. Acad. Sci. USA 92:7440–7444, 1995; Merelli, J. Neurol. 244:450–454, 1997). Although an immune response to this virus is seen during acute exacerbations, the role of HHV-6 infection in MS remains unclear (Soldan et al., Nature Med. 3:1394–1397, 1997).

Current opinion thus favors MS to be an autoimmune disease directed against self neural antigens (Martin et al., Annu. Rev. Immunol. 10:153–169, 1992). To reconcile the role of environment in the pathogenesis of MS as well as the absence of an identifiable infectious pathogen, it is believed that infectious agents may act to trigger an autoimmune process. Such an autoimmune response may result from structural similarities between an infectious agent and neural antigens (antigenic mimicry) or from an expansion of self autoreactive T cell clones in response to bacterial or viral superantigens (Brocke et al., Nature 65:642–646, 1993; Jahnke et al., Science 229:282–284, 1985; Marrack and Kappler, Science 248:325–329, 1998; Oldstone, J. Autoimmun. 2(S):187–194, 1989). Evidence that MS is a disease mediated by T cells that recognize neural antigens has been hard to justify, since measures directed at either eliminating or reducing helper T cell function have not changed the natural history of MS (Sriram and Rodriguez, Neurology 48:469–473, 1997). Improved methods of diagnosing MS would facilitate identification of treatable pathogens and expedite commencement of treatment.

Over the last few years, therapy with β-IFN has emerged as a means of reducing the morbidity of MS. Both β-IFNs (β-1a and β-1b) reduce the number of clinical relapses and slow the progression of the disease. In addition, magnetic resonance imaging (MRI) studies demonstrate a decrease in the number of new inflammatory cerebral lesions in patients receiving β-IFN. Although β-IFN was introduced as a therapeutic agent for MS based on its anti-viral properties, the reasons for the therapeutic benefit of β-IFN for MS remain unclear. Thus far, no viral agent has been consistently found to be associated with MS.

SUMMARY OF THE INVENTION

In a first aspect, the present invention features a method of diagnosing or monitoring multiple sclerosis in an individual, including assaying a test sample from the individual for the presence of Chlamydia, wherein the presence of Chlamydia in the sample indicates the presence of multiple sclerosis.

In preferred embodiments, the Chlamydia is selected from the group consisting of *Chlamydia pneumoniae, Chlamydia pecorum, Chlamydia psittacci*, and *Chlamydia trachomatis*, and the test sample is selected from the group consisting of blood, serum, peripheral blood mononuclear cells, cerebrospinal fluid, urine, nasal secretion, and saliva.

In one embodiment, the test sample is assayed for the presence of Chiamydia by contacting cultured chlamydia-free indicator cells (e.g., HL cells, H292 cells, HeLa cells, or Hep-2 cells) with the test sample; and then detecting the presence of Chlamydia in the cultured indicator cells. The presence of Chlamydia in the cultured indicator cells is indicative of the presence of Chlamydia in the test sample.

The presence of Chlamydia in the cultured indicator cells can be detected by detecting an antibody to Chlamydia (e.g, an antibody to a Chlamydia elementary body antigen), a Chlamydia gene, or a Chlamydia protein in the test sample. The presence of the antibody, gene, or protein is indicative of the presence of Chlamydia in the test sample. In one embodiment, the test sample is incubated under disulfide reducing conditions (e.g., incubating a disulfide reducing agent such as 2,3-dimercaptosuccinic acid, penicillamine, β-lactams, dithiotreitol, mercaptoethylamine, or N-acetylcysteine) prior to detecting the presence of Chlamydia.

In another aspect, the invention features a method of isolating elementary bodies from a receptacle containing elementary bodies. The method includes treating the receptable with trypsin/EDTA to release elementary bodies adhered to the receptacle; and then concentrating the elementary bodies by centrifugation or filtration.

In still another aspect, the invention features a method of releasing DNA from elementary bodies, the method including incubating the elementary bodies under disulfide reducing conditions and digesting the elementary bodies with a protease.

In yet another aspect, the invention features a method of treating an individual diagnosed to have multiple sclerosis, including administering to the individual an effective amount of at least one anti-chlamydial agent. In one embodiment, the individual is administered the antichlamydial agent until the individual tests negative for elementary body phase Chlamydia, replicating phase Chlamydia, and cryptic phase Chlamydia. In another aspect, the individual is administered the anti-chlamydial agent for at least 45 days. The adminstration can be continued for longer periods, and it may be preferable to continue the treatment for at least 90 days, at least 180 days, or even for one year or more.

Preferable anti-chlamydial agents include rifamycins, azalides, macrolides, ketolides, streptogramins, ampicillin, amoxicillin, nitroimidazoles, nitrofurans, quilolones, fluoroquinolones, sulfonamides, isonicotinic congeners, and tetracyclines.

In one embodiment, the individual is also administered an effective amount of an agent that increases inducible nitric oxide synthase (iNOS) activity, such as a type-1 interferon (e.g., α-interferon or β-interferon), a synthetic type-1 interferon analog, or a hybrid type-1 interferon. Preferably, the type-1 interferon analog or hybrid binds to the same receptor as a naturally-occurring type-1 interferon. In another embodiment, the individual is administered at least two anti-chlamydial agents.

In yet another aspect, the invention features a method of treating an individual diagnosed to have multiple sclerosis, including administering to the individual (i) a rifamycin; and (ii) a compound selected from the group consisting of azalides, macrolides, ketolides, and streptogramins. In addition, the individual can optionally be administered ampicillin, amoxicillin, probenecid, a nitroimidazole, a nitrofuran, or any combination thereof.

In another aspect, the invention features a method of treating an individual diagnosed to have multiple sclerosis, including administering to the individual one of the following combinations: a rifamycin, ampicillin or amoxicillin, and probenecid; a quinolone or a fluoroquinolone and a rifamycin; a rifamycin, a sulfonamide, and an isonitotinic congener; or a rifamycin and a tetracycline. The individual can also be administered an effective amount of a compound that increases iNOS activity (e.g., β-interferon).

The administration is preferably continued until the individual tests negative for elementary body phase Chlamydia, replicating phase Chlamydia, and cryptic phase Chlamydia, or for at least 45 days.

In still another aspect, the invention features a pharmaceutical composition that includes one of the following combinations: a rifamycin, ampicillin or amoxicillin, and probenecid; a quinolone or a fluoroquinolone and a rifamycin; a rifamycin, a sulfonamide, and an isonitotinic congener; or a rifamycin and a tetracycline. The composition can optionally include a compound that increases iNOS activity (e.g., β-interferon).

In yet another aspect, the invention features a kit that includes an anti-chlamydial agent and a compound that increases iNOS activity. In a preferred embodiment, the compound that increases iNOS activity is a type-1 interferon (e.g., β-interferon), a synthetic type-1 interferon analog, or a hybrid type-1 interferon, wherein the type-1 interferon analog or hybrid binds to the same receptor as a naturally-occurring type-1 interferon. In another preferred embodiment, the anti-chlamydial agent is selected from the group consisting of rifamycins, azalides, macrolides, ketolides, streptogramins, ampicillin, amoxicillin, nitroimidazoles, quilolones, fluoroquinolones, sulfonamides, isonicotinic congeners, and tetracyclines.

In still another aspect, the invention features a method for determining whether a candidate compound is a potential drug for the treatment of a disease caused or exacerbated by chlamydial infection, the method including the steps of: (a) infecting a non-human animal (e.g., a non-human mammal) with Chiamydia; (b) administering a candidate compound to the animal; and (c) assaying for the presence of a chlamydial infection in a test sample from the mammal. A decrease in the level of infection, relative to the level of infection of a control animal infected with chlamydia but not administered a candidate compound, identifies the candidate compound as a potential drug for the treatment of disease caused or exacerbated by a chlamydial infection. Preferably, the animal is a non-human mammal and brain of the mammal is infected with Chlamydia.

In preferred embodiments, the Chlamydia is selected from the group consisting of *Chlamydia pneumoniae, Chlamydia pecorum, Chlamydia psittacci*, and *Chlamydia trachomatis*, and the test sample is selected from the group consisting of blood, serum, cerebrospinal fluid, urine, nasal secretion, and saliva. In another preferred embodiment, the disease is multiple sclerosis. The animal can be, for example, a mouse, rat, rabbit, or amoeba.

In one embodiment, the test sample is assayed for the presence of Chlamydia by contacting cultured chlamydia-free indicator cells (e.g., HL cells, H292 cells, HeLa cells, or Hep-2 cells) with the test sample; and then detecting the presence of Chlamydia in the cultured indicator cells. The presence of Chlamydia in the cultured indicator cells is indicative of the presence of Chlamydia in the test sample.

The presence of Chlamydia in the cultured indicator cells can also be detected by detecting an antibody to Chlamydia (e.g, an antibody to a Chlamydia elementary body antigen), a Chlamydia gene, or a Chlamydia protein in the test sample. The presence of the antibody, gene, or protein is indicative of the presence of Chlamydia in the test sample. In one embodiment, the test sample is incubated under disulfide reducing conditions (e.g., incubating a disulfide reducing agent such as 2,3-dimercaptosuccinic acid, penicillamine, β-lactams, dithiotreitol, mercaptoethylamine, or N-acetylcysteine) prior to detecting the presence of Chlamydia.

In a related aspect, the invention features a second method for determining whether a candidate compound is a potential drug for the treatment of multiple sclerosis. This method includes the steps of: (a) infecting the brain of a non-human mammal (e.g., a rat, mouse, or rabbit) with Chlamydia; (b) administering a candidate compound to the mammal; and (c) assaying for the loss of white matter in the brain of the mammal, wherein a decrease in the loss of white matter, relative to the loss of white matter in a control mammal infected with chlamydia but not administered any candidate compound, identifies the candidate compound as a potential drug for the treatment of multiple sclerosis.

By "Chlamydia" or "chlamydial cell" is meant any organism of the order Chlamydiales. Examples include, but are not limited to, *C. psittacci, C. trachomatis, C. pecorum, C. abortus, C. caviae, C. felis, C. suis, C. muridarum*, WSU-86-1044, *Parachlamydia acanthamoebae*, and *Simkania negevensis*. By "chlamydial infection" is meant an infection of a cell by a chlamydial cell.

By "indicator cell" is meant a cell capable of being infected by a Chlamydia cell. Preferred indicator cells include HL cells, H292 cells, HeLa cells, and Hep-2 cells, which have been shown to be free of chlamydial infection.

By "long-term therapy" is meant the treatment of a disease (e.g., MS) for at least 45 days, more preferably for at least 60 days or even 90 days, and most preferably for at least 120 days, 180 days, or for a year or more. The long-term therapy can be continued for a given length, or can be stopped when a patient tests negative for elementary body phase Chlamydia, replicating phase Chlamydia, and cryptic phase Chlamydia (e.g., by PCR of a disulfide reducing agent-treated sample from the patient).

It may be desirable to change one or all of the drugs in the middle of the long-term therapy. Changes in drug combinations may be for many reasons, such as to reduce side effects or cost to the patient, or in response to a change in the patient's condition or degree of infection. Moreover, while it is preferable that the therapy is continuous, it is understood that interruption for as much as two weeks or even a month may be desirable or necessary. For example, an individual may take drug combination A for 30 days, stop therapy for two weeks, and then resume therapy (switching to drug combination B) for an additional 30 days. Interrupted therapy and therapy in which one or more drugs are added or removed are each considered to be long-term therapy if the number of days of therapy (i.e., excluding the days in which no drugs for the treatment of MS were administered) is at least 45.

By "anti-chlamydial agent" is meant an agent that results in a decrease in the viability or replication of chlamydial cells at a concentration that would not be substantially detrimental to the cells in which the chlamydial cells were contained. Preferably, the anti-chlamydial agent decreases the viability or replication of chlamydial cells by at least 50%, more preferably by at least 75% and most preferably by at least 90% or even 95%. Preferred anti-chlamydial agents include, without limitation, rifamycins, azalides, macrolides, ketolides, streptogramins, ampicillin, amoxicillin, nitroimidazoles, quilolones, fluoroquinolones, sulfonamides, isonicotinic congeners, and tetracyclines.

The present invention provides methods for the diagnosis of MS with a significant reduction in cost. In addition, these diagnostic assays provide objective data concerning the course of the disease and, thus, the ability to monitor disease progress and the effectiveness of therapy. The invention also provides methods and reagents for the treatment of a patient diagnosed with MS, as well as methods for identifying new drugs for the such treatment.

Other features and advantages of the invention will be apparent from the following description of the preferred embodiments thereof, and from the claims.

BRIEF DESCRIPTION OF THE DRAWINGS

FIGS. 4A and 4B represent SSPE patients #1 and #2, respectively; FIG. 4C represents a patient with CNS syphilis; and FIG. 4D represents a patient with CNS vasculitis. In each figure, lanes 1–3 represent the banding pattern of oligoclonal antibodies following affinity-driven transfer onto untreated (lane 1), measles-antigen coated (lane 2), or *C. pneumoniae* antigen-coated (lane 3) membranes and detection with anti-human IgG antibody.

FIGS. 6A–6E are a series of schematic illustrations showing adsorption studies on CSF immunoglobulins to EB antigens of *C. pneumoniae*, measles, HSV-1, and MBP for five patients with relapsing remitting MS. For each individual patient, the left two lanes represent IEF gel patterns for 0.8 μg Ig of unmanipulated serum and CSF, while the right lanes represent the IEF gel patterns following incubation with antigens. In three patients, the adsorption following incubation with *C. pneumoniae* is incomplete (FIGS. 6A–6C; Arrows indicate some bands of the cathodal antibodies that are adsorbed by *C. pneumoniae* antigens). In two patients, no adsorption of CSF immunoglobulin by *C. pneumoniae* antigen is seen (FIGS. 6D and 6E).

Figure 13A:
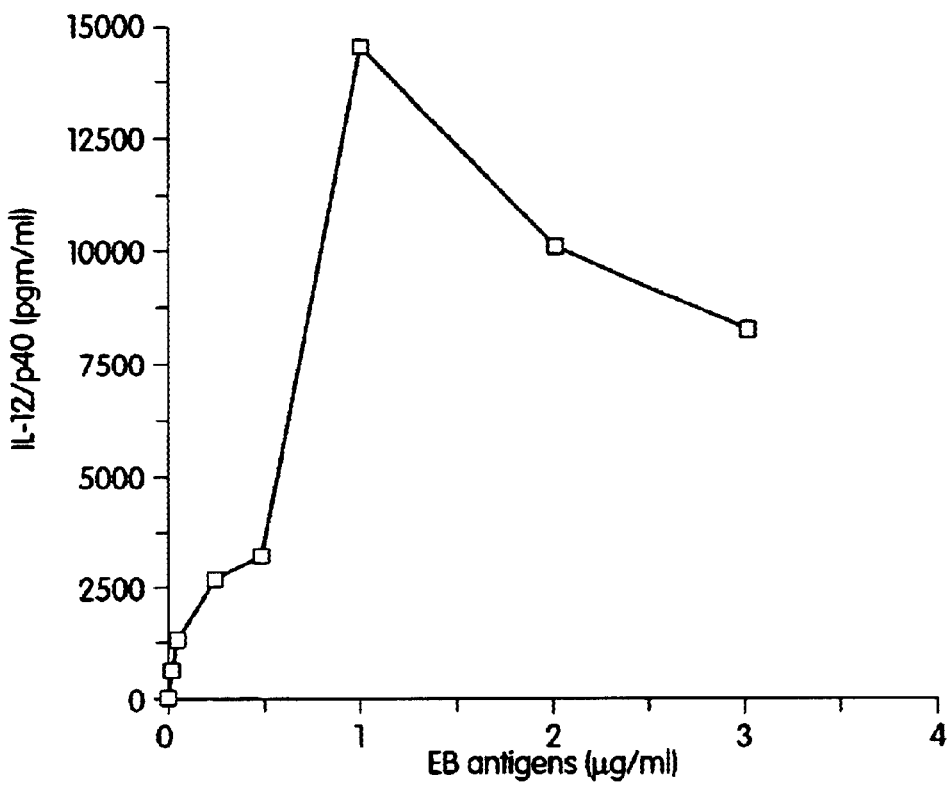
Figure 13B:
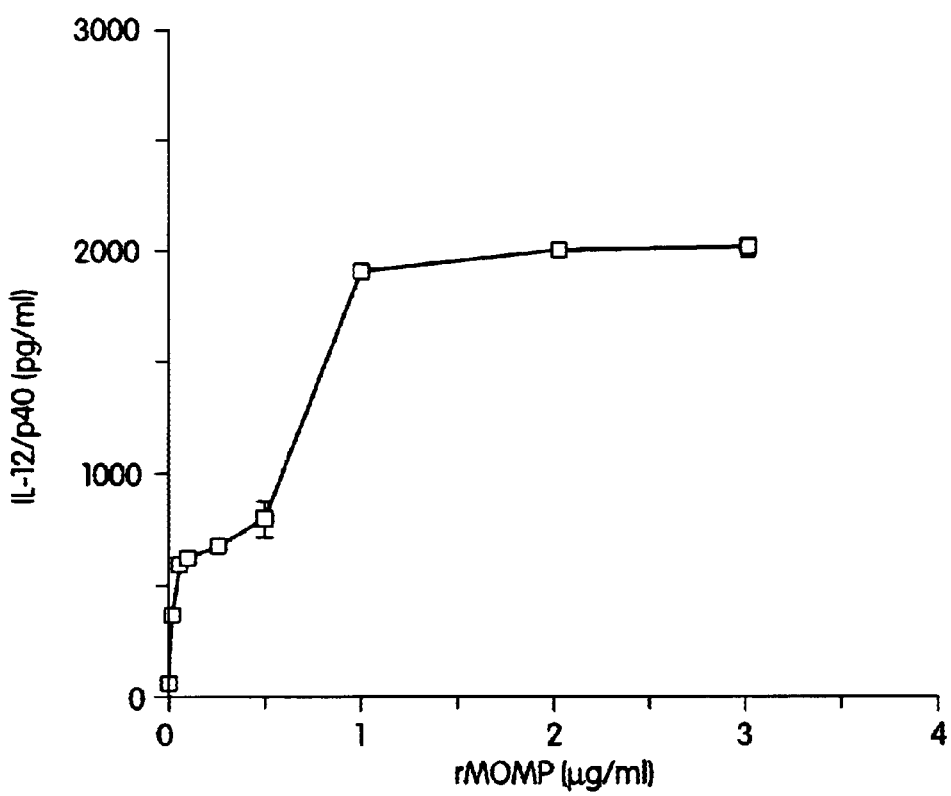

FIGS. 13A and 13B are schematic illustrations showing dose kinetics for induction of IL-12/p40 production after exposure to EB antigens (FIG. 13A) or purified rMOMP (FIG. 13B).

Figure 14:
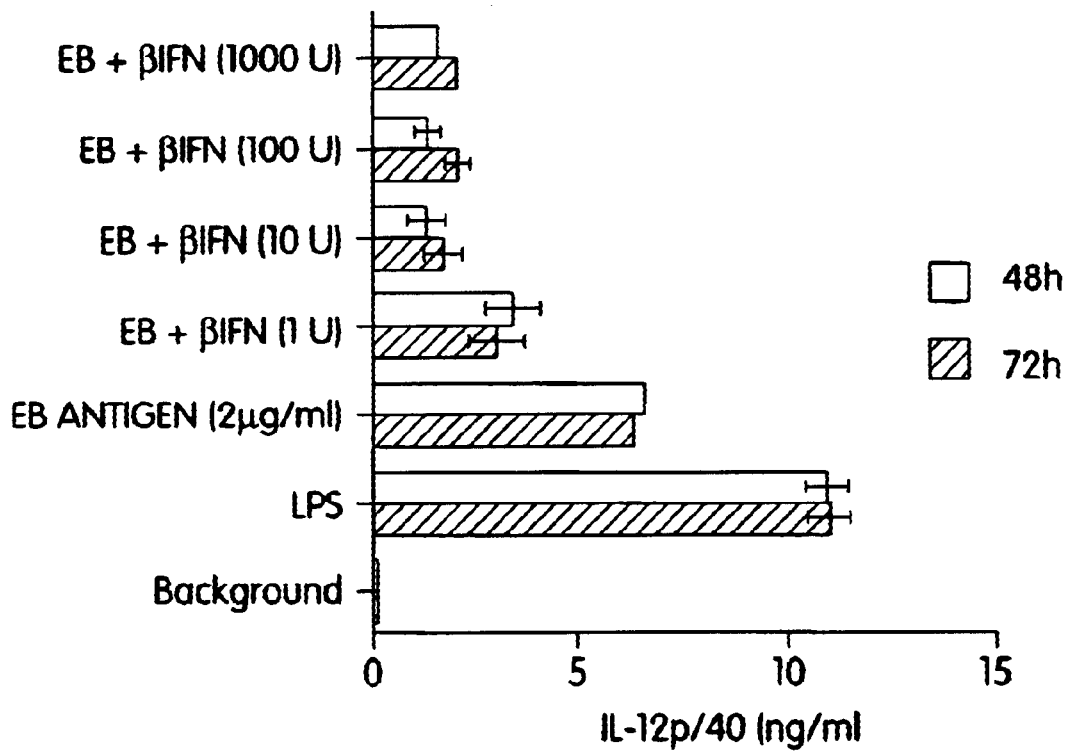

FIG. 14 is a schematic illustration showing inhibition of production of IL-12/p40 in macrophage cultures pretreated with β-IFN and addition of EB antigens.

Figure 15A:
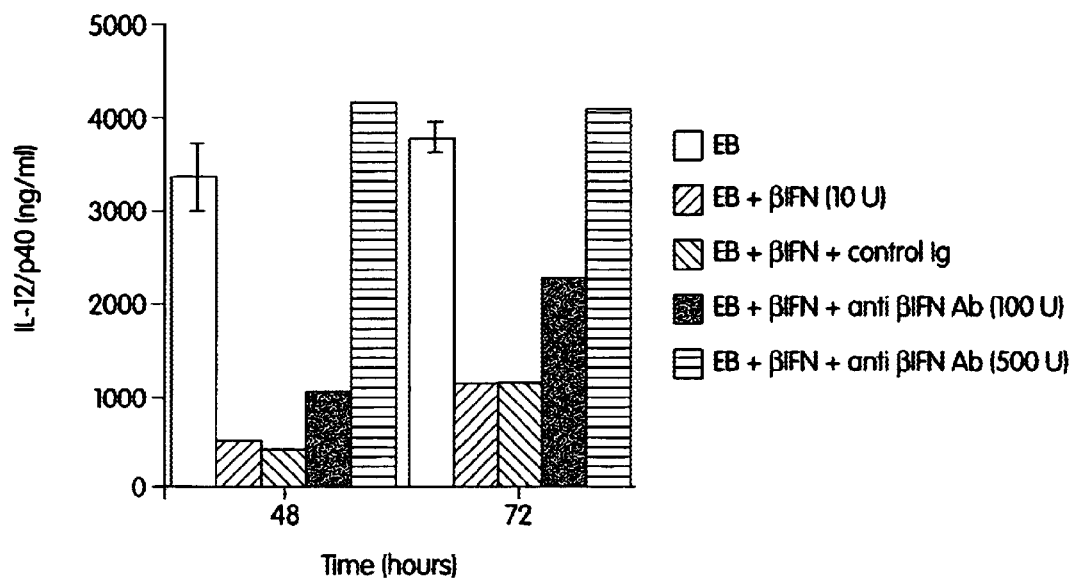
Figure 15B:
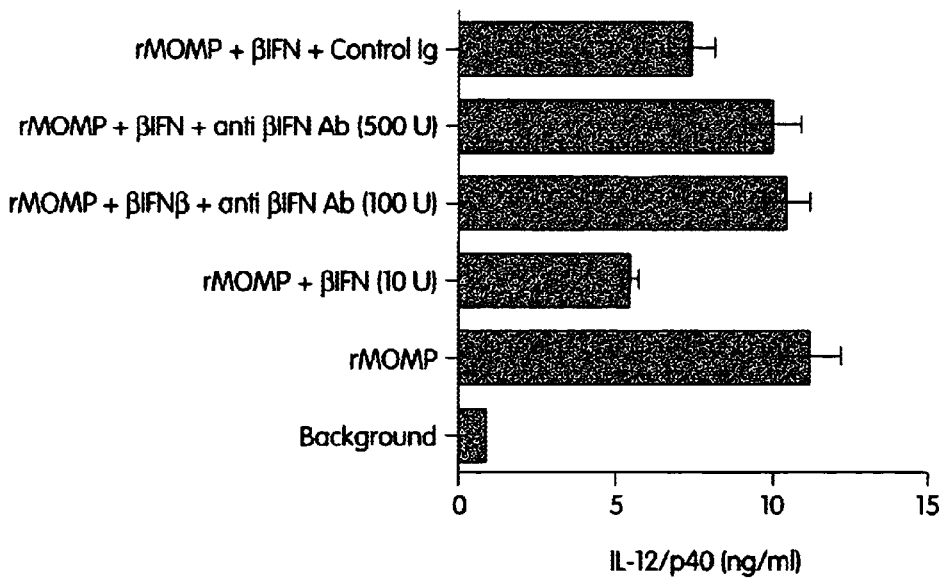

FIGS. 15A and 15B are schematic illustrations showing anti-β-IFN antibody reverses the inhibition of β-IFN on IL-12/p40 production following addition of EB antigens (FIG. 15A) or rMOMP (FIG. 15B).

DETAILED DESCRIPTION

C. pneumoniae belongs to the order Chlamydiales (the members of which are herein referred to collectively as Chlamydia). Members of this order are obligately intracellular pathogens that are infectious to humans and other vertebrates. Other species currently recognized include C. psittacci, C. trachomatis, and C. pecorum. C. psittacci is known to infect microglial cells, while C. pecorum in cattle causes a syndrome known as sporadic bovine encephalomyelitis, for which detailed neuropathologic data are lacking (Storz J., Chlamydia and Chlamydial Induced Diseases. Springfield, Ill.: Charles C. Springer, 1971: 358). C. trachomatis and C. pneumoniae are pathogenic primarily to humans and are recognized to cause latent disease. Meningoencephalitis and other neurological complications have been described in patients with infections due to C. psittaci and C. trachomatis (Korman et al., Clin. Infect. Dis. 25:847–851, 1997). In addition, the Chlamydiales order includes C. abortus, C. caviae, C. felis, C. suis, C. muridarum, WSU-86-1044, Parachlamydia acanthamoebae, and Simkania negevensis (Everett et al. Intl. J. System. Bacteriol. 49:415–440, 1999).

Diagnostic Assays

We have demonstrated a strong correlation between the presence of C. pneumoniae in the CSF of patients with MS by cell culture, polymerase chain reaction (PCR), and immunological methods. C. pneumoniae was isolated from CSF cultures and also was identified in CSF by PCR amplification of the ompA gene of C. pneumoniae. Moreover, CSF titers of IgM and IgG against C. pneumoniae EB antigens were elevated as measured by ELISA methodologies. The specificity of this antibody response for C. pneumoniae was shown by Western blot assays. PCR data in which CSF samples from MS patients and other neurologic diseases (OND) controls were analyzed for the 16S rRNA gene of C. pneumoniae using a nested PCR procedure followed by Southern hybridization with a digoxigenin labeled specific probe also established a link between MS and C. pneumoniae infection. Moreover, IEF/affinity-driven immunoblot assays show that the cationic antibodies in MS patients react to C. pneumoniae EB antigens.

As the presence of Chlamydia correlates with the presence of MS, the invention features a method for diagnosing a patient with MS. In the methods of the invention, a test sample from an individual, such as an individual who is suspected of having MS, is used. The test sample can include blood, serum, cerebrospinal fluid, urine, nasal secretion, saliva, or any other bodily fluid or tissue, or antibodies or nucleic acids isolated from one of the foregoing samples.

The test sample can be assayed for the presence or absence of Chlamydia by culturing the test sample with indicator cells. The indicator cells can be any cells which are capable of being infected by Chlamydia, and which preferably have been shown to be free of infection by Chlamydia and free of elementary bodies of Chlamydia. Representative indicator cells include HL cells, H292 cells, HeLa cells, Hep-2 cells, or any other cell line capable of supporting replication of Chlamydia. The indicator cells are cultured in the presence of the test sample and then assayed for the presence or absence of Chlamydia by an appropriate method, such as by exposing the cultured indicator cells to a detectable antibody that is specific for Chlamydia. The presence of Chlamydia in the cultured indicator cells indicates the presence of Chlamydia in the test sample.

The test sample can also be assayed for the presence or absence of Chlamydia by detecting the presence or absence of a Chlamydia gene (e.g., a gene encoding MOMP, OMP-B, GRO-ES, GRO-EL, DNAK, 16S RNA, 23S RNA, ribonuclease-P, the 76 kD attachment protein, or a KDO-transferase) in the test sample. For example, the test sample can be assayed for the presence or absence of the Chlamydia gene by Southern hybridization using a detectable probe for the appropriate gene. Alternatively, the test sample can be assayed using quantitative PCR or RT-PCR (e.g., by using a LightCycler™ (Idaho Technology Inc., Idaho Falls, Id.) and fluorescent LightCycler™ probes). The presence of the Chlamydia gene in the test sample is indicative of the presence of Chlamydia in the test sample. To facilitate assaying a test sample for the presence or absence of Chlamydia by detecting the presence or absence of a Chlamydia gene, the test sample can be subjected to methods to enhance isolation of Chlamydia elementary bodies from the test sample and to release DNA from the elementary bodies. For example, elementary bodies have a tendency to adhere to the walls of a receptacle containing them; the elementary bodies can be removed from the receptacle by treating the receptacle containing the elementary bodies with trypsin/EDTA, thereby releasing elementary bodies that adhered to the receptacle; and then concentrating the released elementary bodies, such as by centrifugation or filtration. To release DNA from elementary bodies, the elementary bodies are incubated under disulfide reducing conditions, such as incubating the elementary bodies with a disulfide reducing agent such as dithiothreitol (DTT) or 2-mercaptoethanol; and digesting the elementary bodies with a protease.

The test sample can also be assayed for the presence of Chlamydia by detecting the presence of a protein from Chlamydia. For example, the presence of a MOMP protein in the test sample can be detected through the use of ELISA methodologies with an antibody that specifically recognizes the MOMP protein. Alternatively, the test sample may be assayed for the presence of Chlamydia by detecting the presence of antibodies to Chlamydia, or to Chlamydia EB antigens, in the test sample. The presence of Chlamydia protein or antibodies to Chlamydia or Chlamydia EB antigens in the test sample is indicative of the presence of Chlamydia in the test sample. In either of these methods, Chlamydia EB antigens can be prepared by incubating Chlamydia EBs under disulfide reducing conditions, such as in the presence of at least one disulfide reducing agent such as DTT or 2-mercaptoethanol, or another disulfide reducing agent. The presence of proteins or antibodies may be detected by appropriate methods such as by ELISA, Western blot, or isoelectric focusing.

The diagnostic methods described herein are useful for detecting or confirming the disease in a patient, as well as for monitoring the progress of the disease. Disease monitoring is useful, for example, for determining the efficacy of a particular therapy.

Diagnostic Reagents

The invention also provides a diagnostic reagent kit including one or more containers filled with one or more of the ingredients used in the assays of the invention. Optionally associated with such a kit can be a notice in the form prescribed by a governmental agency regulating the manufacture, use, or sale of diagnostic products, which reflects approval by the agency of manufacture, use or sale for human administration. The kit can be labeled with information regarding mode of administration, sequence of execution (e.g., separately, sequentially, or concurrently), or the like. The kit can be a single unit assay or it can be a plurality of unit assays. In particular, the agents can be separated, mixed together in any combination, present in a single vial or tablet. For the purpose of this invention, a unit assay is intended to mean material sufficient to perform only a single assay.

Therapy

In addition to demonstrating that C. pneumoniae infection correlates with MS, we have also found that patients with MS that were treated with anti-chlamydial agents showed improved Expanded Disability Status Scale (EDSS; Kurtzke, Neurology 33:1444–1152, 1983) scores. Thus, it is highly likely that chlamydial infection causes or exacerbates MS. We have also identified combination therapy regimens that, because of the phase of Chlamydia targeted by each drug, are particularly suited for the treatment of MS.

A) Anti-chlamydial Agents

Chlamydia are obligate intracellular bacterial parasites of eukaryotic cells. Members of this order have a unique biphasic development cycle with distinct morphological and functional forms. This developmental growth cycle alternates between (i) intracellular life forms of which two are currently recognized: an intracellular form which can exist as a metabolically-active, replicating organism known as the reticulate body (RB) or a persistent, nonreplicating form known as the cryptic body; and (ii) an extracellular EB form that is infectious and metabolically-inactive.

EBs are small (300 to 400 nm) infectious spore-like forms which are resistant to a variety of physical insults such as enzyme degradation, sonication, and osmotic pressure. This physical stability is likely a result of extensive disulfide cross-linking of the cysteine-rich MOMP. Under the oxidizing conditions of the extracellular milieu of the host, the outer membrane of EBs is relatively impermeable and indestructible.

A number of effective agents that are specifically directed against the initial phase of chlamydial infection (i.e., the transition of the chlamydial EB to a reticulate body (RB)) have been identified. These include compounds in the rifamycin class and act against DNA-dependent RNA polymerase, which is present when the EB begins to transform into the RB phase. Inhibition of this chlamydial DNA-dependent RNA polymerase prevents this transition.

A number of effective agents that are specifically directed against the cryptic growth phase have also been identified. This cryptic growth phase, unlike that of the replicating chlamydial microorganism, which uses host cell energy, involves electrons and electron transfer proteins, as well as nitroreductases. Accordingly, the initial phase of Chlamydia infection is susceptible to the antimicrobial effects of nitroimidazoles, nitrofurans, and other agents directed against anaerobic metabolism in bacteria. Nitroimidazoles and nitrofurans are synthetic antimicrobial agents that are grouped together because both are nitro ($NO_2$—) containing ringed structures and have similar antimicrobial effects. These effects require degradation of the agent within the microbial cell such that electrophilic radicals are formed. These reactive electrophilic intermediates then damage nucleophilic protein sites including ribosomes, DNA, and RNA. Nitroimidazoles and nitrofurans were not previously considered to possess antimicrobial activity against Chlamydia. This apparent lack of antimicrobial activity, however, is due to the fact that conventional susceptibility testing methods only test for effect on the replicating form of Chlamydia, and do not measure the presence of other forms of Chlamydia.

Examples of suitable nitroimidazoles include, but are not limited to, metronidazole, tinidazole, bamnidazole, benznidazole, flunidazole, ipronidazole, misonidazole, moxnidazole, ronidazole, sulnidazole, and their metabolites, analogs, and derivatives thereof. Metronidazole is most preferred. Examples of nitrofurans that can be used include, but are not limited to, nitrofurantoin, nitrofurazone, nifurtimox, nifuratel, nifuradene, nifurdazil, nifurpirinol, nifuratrone, furazolidone, and their metabolites, analogs, and derivatives thereof. Nitrofurantoin is preferred within the class of nitrofurans. Throughout this application and for purposes of this invention, "metabolites" are intended to embrace products of cellular metabolism of a drug in the host (e.g., human or animal) including, but not limited to, the activated forms of prodrugs. The terms "analogs" and "derivatives" are intended to embrace isomers, optically active compounds, and any chemical or physical modification of an agent, such that the modification results in an agent having similar or increased, but not significantly decreased, effectiveness against Chlamydia, compared to the effectiveness of the parent agent from which the analog or derivative is obtained. This comparison can be ascertained using susceptability testing. Cells to be treated can already be cryptically infected or they can be subjected to stringent metabolic or environmental conditions which cause or induce the replicating phase to enter the cryptic phase. Such stringent conditions can include changing environmental/culturing conditions in the instance where the infected cells are exposed to γ-interferon; or by exposing cells to conventional antimicrobial agents (such as macrolides and tetracyclines) which induce this cryptic phase of chlamydial infection in human host cells.

A class of anti-chlamydial agents that is effective against the replicating and cryptic stationary phases of Chlamydia (and possibly against some other stages of the cryptic phase) have been identified. This class of agents includes ethambutol and isonicotinic acid congeners, which include isoniazid (INH), isonicotinic acid (also known as niacin), nicotinic acid, pyrazinamide, ethionamide, and aconiazide. INH is the most preferred compound in this class. Although these compounds were previously considered effective only for mycobacterial infections, we have discovered that these agents, in combination with other antibiotics, are effective against Chlamydia. It is believed that the isonicotinic acid congeners target the constitutive production of catalase and peroxidase, which is a characteristic of microorganisms, such as mycobacteria, that infect monocytes and macrophages. Chlamydia can also successfully infect monocytes and macrophages.

Using INH to eradicate Chlamydia from macrophages and monocytes subsequently assists these cells in their role of fighting infection. These agents appear to be less effective in vitro against the cryptic phase. Thus, ethambutol, INH, and other isonicotinic acid congeners ideally should be used in combination with agents that target other phases of the chlamydial life cycle. These isonicotinic acid congeners are nevertheless excellent agents for the long term therapy of chronic/systemic chlamydial infection.

Adverse conditions, such as limited nutrients, antimicrobial agents, and the host immune response, produce a stringent response in Chlamydia. This stringent response alters the morphological state of the intracellular microorganism and creates dormant forms, including the intracellular EB, which then can cryptically persist until its developmental cycle is reactivated. Conversely, the host cell may lyse and allow the EBs to reach the extracellular milieu. Thus, it is necessary to utilize a combination of agents directed toward the various life stages of Chlamydia and, in particular, against the elementary body for successful management of infection.

During the chlamydial life cycle, it is known that metabolically-inactive spore-like EBs are released into the extracellular milieu. Although these released EBs are infectious, they may not immediately infect nearby susceptible host cells until appropriate conditions for EB infectivity are present. The result of this delay in infection is the extracellular accumulation of metabolically-inactive, yet infectious, EBs. This produces a second type of chlamydial persistance referred to herein as EB "tissue/blood load." This term is similar in concept to HIV load and is defined herein as the number of infectious EBs that reside in the extracellular milieu. Direct microscopic visualization techniques, tissue cell cultures, and polymerase chain reaction test methods have demonstrated that infectious EBs are frequently found in the blood of apparently healthy animals, including humans. This phenomenon is clearly of great clinical importance in chlamydial infections as these metabolically-inactive EBs escape the action of current anti-chlamydial therapy which is directed only against the replicating intracellular forms of Chlamydia. The presence of infectious extracellular EBs after the completion of short term, anti-replicating phase therapy for chlamydial infections has been shown to result in intracellular infection relapse. Thus, the duration and nature of anti-chlamydial therapy required for management of chlamydial infections is, in part, dictated by the extracellular load of EBs. For purposes of this invention, short term therapy can be approximately two to three weeks; long-term therapy, in contrast, may continue for one or several months (see below).

It is also believed that persistance of chlamydial infections may be due in part to the presence of cryptic forms of Chlamydia within the cells. This cryptic intracellular chlamydial form apparently can be activated by certain host factors such as cortisone (Yang et al., Infect. and Immun., 39:655–658, 1983; Malinverni et al., J. Infect. Dis., 172:593–594, 1995). Anti-chlamydial therapy for chronic Chlamydia infections must be continued until any intracellular EBs or other intracellular cryptic forms have been activated and extracellular EBs have infected host cells. This reactivation/reinfection by chlamydial EBs clearly is undesirable as it prolongs the therapy of chlamydial infections, as well as increases the opportunity for antimicrobial resistance to occur.

Physiochemical agents have been identified that can inactivate chiamydial EBs in their respective hosts by reducing disulfide bonds which maintain the integrity of the outer membrane proteins of the EBs. For Chlamydia, disruption of the outer membrane proteins of EBs thereby initiates the transition of the EB form to the RB form. When this occurs in the acellular milieu where there is no available energy source, the nascent RB perishes or falls victim to the immune system. Thus, disulfide reducing agents that can interfere with this process are suitable as compounds for eliminating EBs.

One such class of disulfide reducing agents are thiol-disulfide exchange agents. Examples of these include, but are not limited to, 2,3-dimercaptosuccinic acid (DMSA; also referred to herein as "succimer"); D,L,-β,β-dimethylcysteine (also known as penicillamine); β-lactam agents (e.g., penicillins, penicillin G, ampicillin and amoxicillin, which produce penicillamine as a degradation product), cycloserine, DTT, mercaptoethylamine (e.g., mesna, cysteiamine, dimercaptol), N-acetylcysteine, tiopronin, and glutathione. A particularly effective extracellular anti-chlamydial agent within this class is DMSA, which is a chelating agent having four ionizable hydrogens and two highly charged carboxyl groups which prevent its relative passage through human cell membranes. DMSA thus remains in the extracellular fluid where it can readily encounter extracellular EBs. The two thiol (sulfhydryl) groups on the succimer molecule (DMSA) are able to reduce disulfide bonds in the MOMP of EBs located in the extracellular milieu. Penicillamine can also be used as a disulfide reducing agent to eliminate chlamydial EBs. The use of penicillamine, however, may cause undesirable side effects. Thus, as an alternative, those β-lactam agents which are metabolized or otherwise converted to penicillamine-like agents in vivo (i.e., these agents possess a reducing group) can be orally administered to the human or animal as a means of providing a controlled release of derivative penicillamine, by non-enzymatic acid hydrolysis of the penicillin, under physiologic conditions. Clavulonic acid is not required for this hydrolysis or for using β-lactam agents to create penicillamine in vivo.

As chlamydial RBs transform into EBs, they begin to utilize active transcription of chlamydial DNA and translation of the resulting mRNA. As such, these forms of Chlamydia are susceptible to currently used antimicrobial agents. The anti-chlamydial effectiveness of these agents can be significantly improved by using them in combination with other agents directed at different stages of Chlamydia life cycle, as discussed herein.

Classes of suitable antimicrobial agents include, but are not limited to, rifamycins (also known as ansamacrolides), quinolones, fluoroquinolones, chloramphenicol, sulfonamides/sulfides, azalides, cycloserine, macrolides, ketolides, and tetracyclines. Examples of these agents which are members of these classes, as well as those which are preferred, are illustrated below in Table 1.

TABLE 1

| Drug Class | Examples | Preferred |
| --- | --- | --- |
| Quinolones/ Fluoroquinolones | Ofloxacin Levofloxacin Trovafloxacin Sparfloxacin Norfloxacin Lomefloxacin Cinoxacin Enoxacin Nalidixic Acid Fleroxacin Ciprofloxacin | Levofloxacin |
| Sulfonamides | Sulfamethoxazole | Sulfamethoxazole/ Trimethoprim |
| Azalides | Azithromycin | Azithromycin |

TABLE 1-continued

| Drug Class | Examples | Preferred |
| --- | --- | --- |
| Macrolides | Erythromycin<br>Clarithromycin | Clarithromycin |
| Lincosamides | Lincomycin<br>Clindamycin | Clindamycin |
| Tetracyclines | Tetracycline<br>Doxycycline<br>Minocycline<br>Methacycline<br>Oxytetracyline | Minocycline |
| Rifamycins<br>(Ansamacrolides) | Rifampin<br>Rifabutin | Rifampin |

Members of Chlamydia, including *C. pneumoniae*, were previously considered to be inhibited, and some killed, by the use of a single agent selected from currently used antimicrobial agents such as those described above. We have found, however, that complete eradication of Chlamydia cannot be achieved by the use of any one of these agents alone, unless the administration is of sufficient length (see below), because none are efficacious against all phases of the Chlamydia life cycle and appear to induce a stringent response in Chlamydia, causing the replicating phase to transform into cryptic forms and resulting in a persistent infection that can be demonstrated by PCR techniques which assess the presence or absence of chlamydial DNA. Nevertheless, one or more of these currently used agents, or another agent directed against the replicating phase of Chlamydia, should be included as one of the chlamydial agents in a combination therapy in order to slow or halt the transition of the EB to the RB as well as to inhibit chlamydial replication.

For the treatment of MS, the combinations of antichlamydial agents shown in Table 2 are preferred.

TABLE 2

| Combination | Drug Class | Preferred |
| --- | --- | --- |
| 1 | Rifamycin<br>Azalide<br>Macrolide<br>Ketolide<br>Streptogramin | Rifampin<br>Azithromycin |
| 2 | Rifamycin<br>Ampicillin or Amoxicillin<br>Probenecid | Rifampin |
| 3 | Rifamycin<br>Azalide<br>Macrolide<br>Ketolide<br>Ampicillin or Amoxicillin<br>Probenecid | Rifampin<br><br><br><br>Azithromycin |
| 4 | Rifamycin<br>Azalide<br>Macrolide<br>Ketolide<br>Streptogramin<br>Ampicillin or Amoxicillin<br>Probenecid<br>Nitroimidazole | Rifampin<br>Azithromycin<br><br><br><br><br><br>Metronidazole |
| 5 | Fluoroquinolone<br><br>Rifamycin | Ofloxacin<br>Levoflozacin<br>Rifampin |
| 6 | Sulfonamide<br><br>Rifamycin<br>Isonicotinic congener | Sulfamethoxazole/<br>Trimethoprim<br>Rifampin<br>INH |
| 7 | Rifamycin<br>Tetracycline | Rifampin<br>Minocycline |

To any of the drug combinations, any or all of the following compounds can also be added: probenecid, disulfide reducing agents (e.g., penicillamine), statins (e.g., dantolene), type-1 interferons (e.g., α-IFN or β-IFN), and activators of iNOS activity.

B) Compounds That Increase iNOS Expression or Activity

Nitric oxide (NO) is a relatively unstable free radical synthesized from L-arginine by inducible nitric oxide synthase (iNOS) and is considered to play a role in containing and/or eradicating intracellular pathogens. NO is implicated in a number of in vitro and in vivo models of host resistance to intracellular pathogens such as *Leishmania major, Toxoplasma gondii, Listeria monocytogenes*, and *Mycobacterium tuberculosis*. iNOS may also play a role in inhibiting replication of *C. trachomatis* in epithelial cells. Moreover, disruption of the iNOS gene in mice leads to dissemination of *C. trachomatis*-infected macrophages and delays the clearance of *C. pneumoniae* infections.

We have discovered that heat-killed EBs from *C. pneumoniae* increase iNOS expression, which, as described above, likely helps eradicate intracellular pathogens. Thus, any compound that increases iNOS activity will likely reduce chlamydial infection and improve or maintain neurological function in patients with MS. iNOS activity may be measured, for example, by measuring NO production, nitrate levels, or the level of iNOS mRNA. Preferably, the increase in iNOS activity is by at least 10%, more preferably by at least 25%, and most preferably by 50%, 100%, or more.

C) Type-1 Interferons

We have discovered that β-IFN increases iNOS activity. Based on these findings, it is likely that any type-1 interferon would also increase iNOS activity and, thus, be useful for the treatment of MS.

In accordance with the present invention, a type-1 interferon may be a purified, naturally-occurring, or recombinant subtype, or it may be a hybrid of two or more subtypes or an analog thereof. Further, mixtures containing any two or more of the above may be used in accordance with the present invention. Many variations of the α-IFN and/or β-IFN subtypes, hybrids, and/or analogs may be used. Furthermore, in accordance with the present invention, the α-IFN and/or β-IFN may originate from any mammalian species. Thus, for example, bovine β-IFN subtypes may be used in human therapy.

First, α-IFN and/or β-IFN subtypes may be used which have a length of 166 amino acid units, and which have at least 60% of the consensus sequence shown in Tables 1 and 2 of U.S. Pat. No. 5,780,021, respectively. The remaining portion of the consensus sequence and any portion of or all of the non-consensus portions of any α-IFN or β-IFN may be substituted by any other amino acid, whether naturally occurring or not. By the term "non-consensus" portion or "non-consensus" amino acids is meant those amino acids which do not fall within the amino acids which are sequentially common to α-IFN and/or β-IFNs as shown in Tables 1 and 2 of U.S. Pat. No. 5,780,021. Thus, for example, any α-IFN subtype from Table 1 and/or any β-IFN from Table 2 may be used as a starting model, and up to 40% of the consensus sequence may be substituted and up to 100% of the non-consensus sequence may be substituted by amino acids, such as, for example, glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine, and tryptophan, or even arnithine or citrulline.

Second, α-IFN and/or β-IFN subtypes, hybrids, and/or analogs may be used which are fewer than 166 amino acid residues. In accordance with the present invention, the same rules will apply here as with the first variation above, except that the overall sequence length may be abbreviated to at least 70%, preferably at least 80% (132 or 133 units), and more preferably still to at least 90% (149 or 150 units).

Third, the α-IFN and/or β-IFN subtypes, hybrids, and/or analogs or mixtures thereof may be incorporated as an "active portion" into a larger polypeptide or protein of the formula:

$$\epsilon\text{-}\gamma\text{-}\omega$$

wherein γ is the "active portion" as defined above, and ε and ω each independently represent from 0 to up to about 10,000 amino acids as defined above, with the proviso that the polypeptide or protein has the active portion, γ, topologically available at the surface of the polypeptide or protein in the event that it is folded in a three-dimensional structure. The design of such structures, such that a particular portion is available at the surface of the structure is within the skill of one in the art. Further, in reference to type-1 interferons, the term "analog" means any active portion or sequence described herein having at least 60% of the same amino acids in the same sequence as any sequence described in Table 1 or Table 2 of U.S. Pat. No. 5,780,021.

Generally, the term "interferon" refers to a family of proteins that confer non-specific resistance to a broad range of viral infections, affect cell proliferation, and modulate immune responses. Three major interferons, α-, β- and γ- have been identified based upon antigenic and physicochemical properties, the nature of the inducer, and the cellular source from which they are derived. α-IFN and β-IFN (known collectively as type-1 interferons), are structurally related and compete for the same cell surface receptor. γ-IFN, known as type-2 interferon, is structurally unrelated to type-1 IFNs and is acid labile and has a different cell surface receptor.

α-IFN refers to a family of highly homologous proteins that inhibit viral replication and cellular proliferation and which modulate immune responses. α-IFN is produced by many cells in the body, including peripheral blood leukocytes or lymphoblastoid cells upon exposure to live or inactivated virus, double-stranded RNA, or bacterial products. Moreover, there are multiple subtypes of α-IFN which contain 165–166 amino acids and which have molecular weights of about 18,000 to 20,000 daltons. β-IFN is a cytokine having antiviral, antiproliferative, and immunomodulatory activities. Generally, β-IFN is a glycoprotein containing 166 amino acids having a molecular weight of about 20,000 daltons.

The amount of single subtype of α-IFN or β-IFN, hybrids, analogs or mixtures thereof administered per dose either prior to or after onset of disease is about $1\times10^5$ units to about $7.5\times10^7$ units with administrations being given from once per day to once per week. Amounts may be used, however, which are less than $1\times10^5$ units, such as $5\times10^4$ units or lower, or which are more than $7.5\times10^7$ units, such as $1\times10^8$ units or higher. Of course, the precise amount used will vary, depending upon the judgment of the attending physician, considering such factors as the age, weight, and condition of the patient.

By "consensus sequence" is meant that sequence which is common to all α-IFN or β-IFN subtypes (see Tables 1 and 2 of U.S. Pat. No. 5,780,021).

Table 1 of U.S. Pat. No. 5,780,021 provides a detailed sequence listing of various α-IFN subtypes, showing a consensus sequence for all. In accordance with the present invention, any α-IFN subtype may be used singly or in admixture with others or as hybrids and/or analogs or mixtures thereof as long as it contains at least 60% of the consensus sequence shown in Table 1 as described above or a sequence which exhibits substantially the same α-IFN activity against autoimmune disease as a sequence having at least that portion of the consensus sequence.

Table 2 of U.S. Pat. No. 5,780,021 provides a comparison of detailed sequence listings for β-IFN of human, murine, and bovine origin. In accordance with the present invention, any β-IFN subtype may be used as long as it contains at least 60% of the consensus sequence shown in Table 2 as described above or a sequence which exhibits substantially the same β-IFN activity against autoimmune disease as a sequence having at least the consensus sequence.

Further, hybrid interferons may be constructed and used. Such hybrid interferons are well known (see, for example, Pestka et al., J. Biol. Chem. 257:11497–11502, 1982).

Modes of Administration

The agents of the present invention can be formulated in a physiologically acceptable vehicle in a form which will be dependent upon the method by which it is administered. In one aspect, the invention pertains to a combination of agents, each of which is targeted against a different phase of the chlamydial life cycle or enhances the anti-chlamydial activity of other agents. The combination of agents can be used in the management of chlamydial infection or prophylaxis thereof to prevent recurrent infection. The combination of agents can be in the form of an admixture, as a kit, or individually, and/or by virtue of the instruction to produce such a combination. It is understood that combination therapy can include multiple agents that are effective within a particular phase of the chlamydial life cycle. The combination of agents can also include immunosuppressants, anti-inflammatory agents, vitamin C, or combinations thereof.

The therapeutic methods described herein can be used to ameliorate or stabilize conditions/symptoms associated with MS, when the disease is caused or aggravated by chlamydial infection. Compounds and agents described herein can be administered to an individual using standard methods and modes which are typically routine for the disease state. While any mammal may be treated, such as dogs, cats, cows, pigs, horses, or poultry, it is particularly desirable that the mammal treated be human.

Combinations of agents of this invention can be used for the manufacture of a medicament for simultaneous, separate, or sequential use in managing chlamydial infection or prophylaxis thereof. The agents can also be used for the manufacture of a medicament for the treatment of MS. The agents can be administered subcutaneously, intravenously, parenterally, intraperitoneally, intradermally, intramuscularly, topically, enteral (e.g., orally), sublingually, rectally, nasally, buccally, vaginally, by inhalation spray, by drug pump or via an implanted reservoir in dosage formulations containing conventional non-toxic, physiologically acceptable carriers or vehicles. The preferred method of administration is by oral delivery. The form in which it is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, nose drops, aerosols, inhalants, nebulizers, eye drops, or suppositories can be used. The compounds and agents of this invention can be administered together with other biologically active agents.

In a specific embodiment, it may be desirable to administer the agents of the invention to the brain; this may be achieved by, for example, and not by way of limitation, local infusion during surgery, by injection, by means of a catheter, by means of a suppository, or by means of an implant (e.g., a porous, non-porous, or gelatinous material, including membranes, such as sialastic membranes or fibers). When it is desirable to direct the drug to the central nervous system, techniques which can opportunistically open the blood brain barrier for a time adequate to deliver the drug there through can be used. For example, a composition of 5% mannitose and water can be used.

The present invention also provides pharmaceutical compositions. Such compositions include a therapeutically (or prophylactically) effective amount of the agent, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

Suitable pharmaceutically acceptable carriers include, but are not limited to, water, salt solutions (e.g., NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, and polyvinyl pyrolidone. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of agents which will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions and/or adjunct therapies of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

The invention will be further illustrated by the following non-limiting examples of diagnostic and therapeutic methods.

EXAMPLE 1

Identification of the Presence of *C. pneumoniae* in Individuals with MS

A) Methods

Patient Population

The study evaluated 17 patients with relapsing remitting MS (4M/13F, mean age 31 years) at the time of diagnosis of clinically definite disease (Table 3) and 20 patients with progressive MS (10M/10F, mean age 40 years) (Table 4). Among the 17 relapsing remitting MS patients, two patients were on β-IFN that was instituted four weeks and 16 weeks, respectively, prior to the enlistment of these patients for the lumbar puncture. Both patients (#5 and #14) were also recovering from a recent clinical worsening. The remaining 15 patients were not on any immunosuppressive or immunomodulatory drugs. All except three of these 17 MS patients had oligoclonal bands in the CSF (Table 3). Among the patients with progressive disease, two had primary progressive disease, four had relapses with sequelae (relapsing progressive disease), and the remaining 14 had secondary progressive disease. Four of these 20 MS patients were on β-IFN, and three were on methotrexate at the time the lumbar puncture was performed. All except two of these 20 MS patients had oligoclonal bands in the CSF (Table 4). Twenty-seven patients (12M/15F, mean age 39 years) with other neurological diseases (OND) were selected as controls (Table 5). Of these, 19 had CSF abnormalities (i.e., increased CSF protein and/or increase in CSF lymphocytes) consistent with either a break in the blood-CSF or blood-brain barrier. One patient (#6) with chronic meningitis of unknown etiology had oligoclonal bands in the CSF. Of the remaining seven OND control patients with normal CSF profiles, two were diagnosed with cerebrovascular disease and one case each was seen with brain abscess, Hashimoto's encephalopathy, polyneuropathy, Wernike-Korsakoff's encephalopathy, and a syndrome consistent with vasculitis and stroke.

TABLE 3

| Patient Number | Age/Sex | Time from Onset of 1st symptom to Dx | EDSS | CSF Protein Concentration; CSF Cell count | CSF Ig Index | Oligoclonal Bands | CSF Culture | CSF PCR/S |
|---|---|---|---|---|---|---|---|---|
| 1 | 26/F | 1 year | 1.5 | 32 mg/dl; 4 cell/µl | 1.28 | Present | Negative | Positive |
| 2 | 47/F | 2 months | 3.0 | 47 mg/dl; 7 cell/µl | 1.09 | Present | Positive | Positive |
| 3 | 22/F | 2 years | 1.5 | 40 mg/dl; 11 cell/µl | 0.60 | Present | Negative | Positive |
| 4 | 51/F | 3 years | 1.5 | 32 mg/dl; 0 cells/µl | 0.61 | Present | Negative | Positive |
| 5 | 22/F | 6 months | 6.0 | 34 mg/dl; 10 cell/µl | 0.90 | Present | Positive | Positive |
| 6 | 20/F | 3 months | 1.0 | 24 mg/dl; 9 cell/µl | 1.42 | Present | Negative | Positive |
| 7 | 49/M | 1 year | 3.5 | 57 mg/dl; 4 cell/µl | 1.44 | Present | Positive | Positive |
| 8 | 50/M | 6 months | 3.5 | 86 mg/dl; 2 cell/µl | 1.22 | Present | Positive | Positive |
| 9 | 39/F | 6 months | 2.0 | 53 mg/dl; 0 cells/µl | 0.55 | Absent | Negative | Positive |
| 10 | 29/F | 12 years | 3.5 | 22 mg/dl; 0 cells/µl | 0.48 | Absent | Negative | Positive |
| 11 | 28/F | 4 months | 1.5 | 68 mg/dl; 1 cell/µl | 0.5 | Absent | Positive | Positive |
| 12 | 27/F | 4 years | 2.5 | 45 mg/dl; 2 cells/µl | 1.97 | Present | Negative | Positive |
| 13 | 49/F | 1.5 years | 2.5 | 55 mg/dl; 2 cell/µl | 1.60 | Present | Negative | Positive |
| 14 | 47/M | 2 years | 5.5 | 82 mg/dl; 14 cells/µl | 0.67 | Present | Negative | Positive |
| 15 | 26/F | 6 months | 3.0 | 20 mg/dl; 6 cell/µl | 1.19 | Present | Positive | Positive |
| 16 | 40/F | 22 years | 2.0 | 33 mg/dl; 1 cell/µl | 0.88 | Present | Negative | Positive |
| 17 | 44/M | 6 months | 3.0 | 24 mg/dl; 3 cell/µl | 0.46 | Absent | Positive | Positive |

TABLE 4

| Patient Number | Age/Sex | Age of Onset | EDSS | Immuno-modulatory Drugs | CSF Protein Concentration; CSF Cell count | CSF Ig Index | Oligoclonal Bands | CSF Culture | CSF PCR/S | CSF Ig vs EBs by Western Blot |
|---|---|---|---|---|---|---|---|---|---|---|
| 1 | 35/M | 30 | 4.0 | None | 53 mg/dl; 2 cells/µl | 1.07 | Present | Positive | Positive | Positive |
| 2 | 51/M | 31 | 7.5 | None | 69 mg/dl; 0 cells/µl | 0.5 | Present | Positive | Positive | Positive |
| 3 | 40/M | 38 | 6.5 | None | 85 mg/dl; 4 cells/µl | 0.64 | Present | Negative | Positive | Positive |
| 4 | 42/F | 38 | 6.0 | IFN 1 alpha | 18 mg/dl; 3 cells/µl | 1.73 | Present | Negative | Positive | Weakly Positive |
| 5 | 42/F | 33 | 7.0 | None | 37 mg/dl; 2 cells/µl | 2.69 | Present | Positive | Positive | Positive |
| 6 | 47/M | 33 | 7.0 | None | 112 mg/dl; 2 cells/µl | 0.58 | Present | Positive | Positive | Positive |
| 7 | 35/F | 29 | 7.0 | None | 48 mg/dl; 2 cells/µl | 3.69 | Present | Positive | Positive | Positive |
| 8 | 31/M | 25 | 5.0 | None | 41 mg/dl; 1 cells/µl | 0.5 | Absent | Positive | Positive | Weakly Positive |
| 9 | 50/M | 40 | 6.5 | MTX | 24 mg/dl; 3 cells/µl | 0.6 | Present | Positive | Negative | Weakly Positive |
| 10 | 37/F | 34 | 3.5 | None | 34 mg/dl; 15 cells/µl | 0.77 | Present | Present | Positive | Weakly Positive |
| 11 | 54/M | 44 | 8.5 | MTX | 82 mg/dl; 15 cells/µl | 1.39 | Present | Positive | Positive | Positive |
| 12 | 29/F | 21 | 8.0 | IFN 1 beta | 14 mg/dl; 1 cells/µl | 0.8 | Present | Positive | Positive | Weakly Positive |
| 13 | 44/F | 23 | 7.5 | None | 59 mg/dl; 1 cells/µl | 0.7 | Present | Positive | Positive | Positive |
| 14 | 36/M | 32 | 4.5 | MTX | 31 mg/dl; 0 cells/µl | 0.52 | Absent | Negative | Positive | Negative |
| 15 | 42/F | 38 | 3.5 | None | 32 mg/dl; 0 cells/µl | 0.6 | Present | Positive | Positive | Weakly Positive |
| 16 | 54/F | 40 | 6.5 | None | 54 mg/dl; 4 cells/µl | 1.4 | Present | Negative | Positive | Positive |
| 17 | 43/M | 21 | 6.0 | IFN 1 beta | 54 mg/dl; 4 cells/µl | ND | Present | Positive | Positive | Positive |
| 18 | 28/M | 18 | 4.5 | IFN 1 beta | 33 mg/dl; 2 cells/µl | 1.2 | Present | Present | Positive | Positive |
| 19 | 48/F | 24 | 8.5 | None | 48 mg/dl; 5 cells/µl | 0.7 | Present | Positive | Positive | Positive |
| 20 | 34/M | 32 | 6.0 | None | 115 mg/dl; 30 cells/µl | 0.5 | Present | Positive | Positive | Positive |

TABLE 5

| Patient Number | Age/Sex | Neurologic Diagnosis | CSF Protein Concentration; CSF Cell count | CSF Ig Index | Oligoclonal Bands | CSF Culture | CSF PCR/S | CSF Ig vs EBs by Western Blot |
|---|---|---|---|---|---|---|---|---|
| 1 | 44/F | AIDP | 121 mg/dl; 0 cells/µl | 0.2 | Absent | Negative | Positive | Weakly Positive |
| 2 | 65/M | CNS Wegener's | 35 mg/dl; 2 cells/µl | 0.5 | Absent | Negative | Negative | Negative |
| 3 | 19/F | Encephalitis | 18 mg/dl; 15 cells/µl | ND | Absent | Negative | Negative | Negative |
| 4 | 32/M | CNS Vasculitis | 121 mg/dl; 0 cells/µl | 2.6 | Absent | Negative | Negative | Negative |
| 5 | 36/F | Paraneoplastic Encephalitis | 104 mg/dl; 13 cells/µl | 0.5 | Present | Negative | Negative | Weakly Positive |
| 6 | 25/M | Chronic Meningitis | 155 mg/dl; 227 cells/µl | 0.5 | Present | Negative | Negative | Negative |
| 7 | 41/F | Granulomatous Angitis | 88 mg/dl; 10 cells/µl | 0.5 | Absent | Negative | Negative | Negative |
| 8 | 32/F | PIE | 95 mg/dl; 103 cells/µl | 0.47 | Absent | Positive | Negative | Weakly Positive |

TABLE 5-continued

| Patient Number | Age/Sex | Neurologic Diagnosis | CSF Protein Concentration; CSF Cell count | CSF Ig Index | Oligoclonal Bands | CSF Culture | CSF PCR/S | CSF Ig vs EBs by Western Blot |
|---|---|---|---|---|---|---|---|---|
| 9 | 39/F | Polyneuropathy | 54 mg/dl; 0 cells/μl | 0.5 | Absent | Negative | Negative | Negative |
| 10 | 59/F | CNS Venous Thrombosis | 72 mg/dl; 7 cells/μl | 0.55 | Absent | Negative | Negative | Negative |
| 11 | 66/F | Brain Abscess | 31 mg/dl; 2 cells/μl | 0.37 | Absent | Negative | Negative | Negative |
| 12 | 28/M | CNS Vasculitis | 30 mg/dl; 8 cells/μl | 0.4 | Absent | Negative | Negative | Negative |
| 13 | 24/F | CNS Vasculitis | 53 mg/dl; 0 cells/μl | 0.4 | Absent | Negative | Negative | Negative |
| 14 | 80/F | CNS Wegener's | 63 mg/dl; 11 cells/μl | ND | ND | Negative | Negative | Negative |
| 15 | 44/M | Hydrocephalus | 146 mg/dl; 14 cells/μl | 0.38 | Absent | Negative | Negative | Negative |
| 16 | 38/F | HSV-2 Myelitis | 74 mg/dl; 4 cells/μl | 0.2 | ND | Negative | Negative | Negative |
| 17 | 50/F | Encephalopathy | 25 mg/dl; 2 cells/μl | ND | Absent | Negative | Negative | Weakly Positive |
| 18 | 34/M | Thoracic Myelitis | 59 mg/dl; 21 cells/μl | 0.48 | Absent | Negative | Positive | Negative |
| 19 | 36/F | Brain Tumor | 137 mg/dl; 6 cells/μl | 0.48 | Absent | Negative | Positive | Negative |
| 20 | 54/M | Stroke | 44 mg/dl; 0 cells/μl | ND | ND | Negative | Negative | Negative |
| 21 | 52/F | Myelitis | 51 mg/dl; 2 cells/μl | 0.50 | Absent | Positive | Positive | Negative |
| 22 | 36/F | Aseptic Meningitis | 39 mg/dl; 13 cells/μl | 0.38 | Absent | Negative | Negative | Negative |
| 23 | 41/F | HSV-2 Myelitis | 58 mg/dl; 0 cells/μl | 0.54 | Absent | Positive | Positive | Negative |
| 24 | 36/F | CNS Lupus | 57 mg/dl; 0 cells/μl | 0.46 | Absent | Negative | Negative | Negative |
| 25 | 28/F | Vasculitis | 58 mg/dl; 1 cells/μl | 0.49 | Absent | Negative | Negative | Negative |
| 26 | 38/M | Lumbrosacral Plexopathy | 62 mg/dl; 0 cells/μl | 0.47 | Absent | Negative | Negative | Negative |
| 27 | 62/M | W-K Encephalopathy | 50 mg/dl; 0 cells/μl | ND | Absent | Negative | Negative | ND |

Culture of *C. pneumoniae* From CSF

To at least 300 μl of a recently collected CSF sample, 200 μl of trypsin (0.25%) ethylenediaminetetraacetic acid (1 mM) (EDTA; GIBCO BRL, Gaithersburg, Md.) in Hank's balanced salt solution (HBSS; GIBCO) at pH 7.2 was added to achieve a final concentration of 0.1% trypsin; the sample was vortexed and then incubated at 37° C. for 30 minutes. Following incubation, the sample was again vortexed, centrifuged for 45 minutes at 12,000×g in a microcentrifuge, and the pellet resuspended in 1 ml of Iscoves medium (GIBCO); 0.5 ml of this diluted CSF sample was added to HL indicator cells (Human Lung Carcinoma Cells, Washington Research Foundation, Seattle, Wash.) in each of two shell vials. Prior to adding the CSF sample, it is preferable that indicator HL cells be demonstrated to be free of cryptic infection by *C. pneumoniae*. HL cells were established as confluent monolayers on 12 mm cover slips, washed with HBSS four times, treated with diethylaminoethyl-dextran (30 μg/ml) (DEAE-Dextran; GIBCO) in HBSS for 15 minutes, and washed again four times with HBSS. After the CSF sample was added, the shell vials were centrifuged at 4° C. at 1,800×g for one hour. To the spun shell vials was added 1 ml of Iscoves or RPMI medium (GIBCO) containing 4 μg/ml cyclohexamide, 20% fetal calf serum (FCS; Hyclone, Logan, Utah) demonstrated to be free of *C. pneumoniae* and EBs, 4 mM L-glutamine (Sigma, St Louis, Mo.), and 100 μg/ml gentamicin (Sigma); the vials were then incubated at 35° C. for seven days with additional centrifugation (4° C. at 1,800×g for 1 hour) on days 4, 5, and 6. Continuous propagation for 14 days was achieved by a single culture passage after seven days, followed by a second incubation period of seven days. One cover slip of the duplicate shell vials was examined for *C. pneumoniae* inclusions after each incubation period. Following fixation, the cell monolayer was stained with a *C. pneumoniae*-specific fluorescene-conjugated mouse monoclonal antibody (1:50 dilution; Washington Research Foundation) and Evan's blue (3 μl/ml) in HBSS containing 1% BSA, 0.15% Tween 20, or by an analogous immunocytochemical staining method. Enumeration of HL cells containing *C. pneumoniae* inclusions was done under epi-fluorescence using a Nikon Diaphot-TMD microscope with a B filter cassette. In the presence of Evans blue counter stain, the emission spectrum was shifted toward the infrared for this particular monoclonal antibody. Alternatively, a regular light microscope may be used for inclusion bodies stained by immunocytochemical methods.

For passage, the remaining vial was sonicated to remove the cells from the cover slip after which EDTA to 1 mM final concentration was added. This vial was incubated at 37° C. for 30 minutes, centrifuged at low speed (600×g for 5 min) to remove cell debris, and the supernatant was centrifuged at 12,000×g for 45 min at ambient temperature. The pellet was resuspended in 1 ml of Iscoves and 0.5 ml used to inoculate each of duplicate fresh DEAE-Dextran-treated monolayers. This subculture was centrifuged at 4° C. at 1,800×g for one hour at the time of subculture as well as again on days 4, 5, and 6. As a quality control measure for this and all other laboratory methods, cell lines, FCS, media, or reagents of any type must be determined to be *C. pneumoniae*-free by PCR/Southern hybridization assay. All manipulations of CSF samples and/or shell vials in which contamination might occur were done in laminar-flow hoods (BL3) under continuous ultraviolet light.

PCR Amplification of Genes From *C. pneumoniae*

The MOMP Gene

To at least 300 μl of CSF sample, 200 μl of HBSS containing 0.25% trypsin and 1 mM EDTA at pH 7.2 was added to achieve a final concentration of 0.1% trypsin, and the sample vortexed and then incubated at 37° C. for 30 minutes. Following incubation, the sample was again vortexed, centrifuged for 45 minutes at 12,000×g in a microcentrifuge, and the pellet resuspended in 20 μl of lysis buffer (0.5% sodium dodecylsulfate (SDS), 1% NP40, 0.2 M NaCl, 10 μM DTT, 10 mM EDTA, 20 mM Tris-HCl at pH 7.5). To this was added 8 μl of proteinase K (20 μg/ml; Boehringer-Mannheim, Indianapolis, Ind.), after which the specimen was mixed and incubated overnight at 37° C. From this specimen, purified DNA was extracted from the aqueous fraction with Na acetate (1:10 dilution by volume of a 3 M solution; Fisher Scientific, Pittsburgh, Pa.) and mixing/ precipitation with 2:2.5 dilution by volume of cold absolute ethanol after performing initial extraction with a mixture of phenol:chloroform:isoamyl alcohol (25:24:1; Sigma Chemical, St. Louis, Mo.) followed by two extractions with chloroform. The DNA was washed with 70% ethanol in water, spun (600×g for 5 minutes at ambient temperature), and resuspended in 20 μl of water.

PCR was carried out using the entire MOMP gene (1.2 kb) using Deep Vent polymerase in the manufacturer's buffer (New England Biolabs, Boston, Mass.) with no additional $MgCl_2$. The MOMP primers were as follows. MOMP forward: ATG AAA AAA CTC TTA AAG TCG GCG TTA TTA TCC GCC GC (SEQ ID NO: 1); MOMP reverse: TTA GAA TCT GAA CTG ACC AGA TAC GTG AGC AGC TCT CTC G (SEQ ID NO: 2). Reaction mixtures contained 20 μl of target DNA, 200 picoMoles each primer, 200 μM each dNTP, and 1 unit of Deep Vent polymerase. The PCR reaction was carried out for 35 cycles at 94° C. for 1 minutes, 58° C. for 2 minutes, and 74° C. for 3 minutes. PCR reactions were analyzed by electrophoresis in 1% agarose gel for 45 minutes at 95 volts. For confirmation and enhanced sensitivity, the gels were further analyzed by Southern hybridization using a digoxigenin-labeled (DIG, Boehringer-Mannheim) MOMP gene probe from the TWAR strain of *C. pneumoniae* (ATCC VR-1310). Briefly, agarose gels were treated with 0.4 M NaOH for 15 minutes, and the DNA transferred by capillary blotting to positively charged nylon membranes (Boehringer-Mannheim). The TWAR MOMP gene was labeled with DIG (Boehringer-Mannheim). Membranes were prehybridized in hybridization buffer (10% Dextran sulfate, 1M NaCl, 1% SDS) for at least one hour at 65° C. DIG-labeled probe (100 ng) was added in fresh hybridization buffer and incubated at 65° C. overnight. Blots were washed 3 times in 2×SSC, 1% SDS at ambient temperature, and an additional three times at 65° C. Final high stringency washes were performed in 0.1×SSC, 0.1% SDS at ambient temperature. Membranes were blocked in 5% w/v dehydrated non-fat milk in PBS, 0.2% Tween 20 for one hour at ambient temperature, then incubated in anti-DIG-alkaline phosphatase conjugated Fab fragments (Boehringer-Mannheim) diluted 1:5000 in PBS, 0.2% Tween 20, and developed with NBT/BCIP substrate.

Nested PCR primers were chosen within the MOMP which are *C. pneumoniae* specific (located in variable domains 1 and 4) and yield a 727 bp band. These primers are as follows. Nest MOMP forward: GCT GCT GCA AAC TAT ACT ACT GCC (SEQ ID NO: 3); Nest MOMP reverse: GAA TCA GTA GTA GAC AAT GCT GTG G (SEQ ID NO:4). The target for the nested primers was 5:1 of PCR product from the full length MOMP reaction. The nested PCR reaction was carried out under the same reaction conditions used for the full length MOMP: 35 cycles at 94° C. for 1 minute, 45° C. for 2 minutes, and 72° C. for 3 minutes, including a 7 minute extension at 72° C. at the end of the program. PCR reactions were analyzed by electrophoresis in 1% agarose gel for 45 minutes at 95 volts. For confirmation and enhanced sensitivity of the nested PCR, the nested PCR gels were further analyzed by Southern hybridization using a DIG-labeled MOMP probe from the TWAR strain of *C. pneumoniae.*

Measurement of Antibody Levels in CSF to Whole Elementary Body Antigens of *C. pneumoniae* by ELISA.

CSF antibodies to *C. pneumoniae* were measured by an ELISA technique as follows. 96-well plates were coated with 100 μl of *C. pneumoniae* EB antigens (250 ng/well). EB antigens were prepared from concentrated *C. pneumoniae* EBs by treating them with 25 mM DTT, 2% 2-mercaptoethanol, and 2% SDS for five minutes at 100° C. Treated EBs were sonicated, centrifuged (500×g for 30 min at room temperature) and resuspended (2 μg/ml protein) in PBS pH 7.4. Concentrated *C. pneumoniae* EBs were obtained by growing *C. pneumoniae* ATTC VR-1310 or other isolates in 25 ml flasks containing a confluent growth of HL cells (Washington University Foundation) in Dulbecco's minimal essential medium (DMEM; GIBCO) and 10% FCS. Infection was facilitated by two washes with HBSS followed by a 20 minute preincubation with DEAE-Dextran (30 μg/ml) in HBSS. The infectious inoculum was added in 2 ml volume of serum-free media and the flasks centrifuged at 1,200×g for one hour at 4° C. To the spun flasks was added 2 ml of Iscoves medium containing 4 μg/ml cyclohexamide, 20% FCS, 4 mM L-glutamine, and 100 μg/ml gentamicin. The flasks were then incubated at 35° C. for three days at which time the infected cells began to lyse and release EBs. On day 4, the culture flasks were sonicated for 20 seconds, and the cell debris removed by centrifugation at 600×g for five minutes at room temperature. The supernatant containing the infectious EBs was centrifuiged at 18,000×g for 30 minutes and the pellet resolubilized in water containing 25 mM DTT, 2% 2-mercaptoethanol, and 2% SDS. After the EB antigens were added to the 96-well plate, the plates were incubated overnight and then unoccupied sites in the wells blocked with 1% BSA, PBS-Tween 20 for one hour. The CSF samples were added to each well in a final concentration of 1 μg of immunoglobulin diluted in 100 μl of PBS as determined by rate laser nephelometric methods (Behring Nephelometer Analyzer II, Behring Diagnostics Inc, San Jose, Calif.) and incubated overnight at 4° C. Following this step, the plates were washed with PBS-Tween 20, and then peroxidase-conjugated goat anti-human IgG (1:10,000) (Sigma) was added. Following two hours of incubation, the plates were washed with PBS-Tween 20 and the substrate added. The absorbance units at 405 nm were read using an ELISA reader (Bio-Tech Instruments, Burlington, Vt.) at 1 hour.

Western Blot Assays of Elementary Body Antigens Reactive Against CSF Immunoglobulins EB antigens were prepared from concentrated *C. pneumoniae* EBs by treating them with 25 mM DTT, 2% 2-mercaptoethanol, and 2% SDS for 5 minutes at 100° C. as done for the ELISA procedure. Treated EBs were sonicated, and then 2.5 μg of the sonicated protein was loaded in each well and run on an 8% SDS-PAGE gel at 100V for two hours at ambient temperature. The gel was transferred to nitrocellulose membrane at 100V for one hour at ambient temperature. Individual strips were cut and incubated in 3% BSA-tris-buffered saline with Tween 20 (TBST) for two hours at ambient temperature to block unoccupied sites. The strips were then washed three times with TBST, and finally incubated with CSF (containing 5 μg of immunoglobulin) for two days at 4° C. Following incubation with CSF, the strips were washed three times with TBST and incubated with peroxidase-conjugated goat anti-human IgG (1:500) (Sigma) for 1.5 hours at ambient temperature and examined using a chemiluminiscent detection assay (Pierce, Rockford, Ill.). Controls use cell lysates of uninfected HL cells instead of *C. pneumoniae* EBs in Western blot assays.

B) Results

Detection of *C. pneumoniae* in CSF

Direct evidence for the presence of *C. pneumoniae* in the CNS was determined by CSF cultures. The majority of cultures were read as positive after the second passage. Cultivation and isolation of *C. pneumoniae* was performed according to a rigorous protocol designed to maximize yield. Among patients with newly diagnosed relapsing remitting MS, 47% of patients (8/17) had *C. pneumoniae* isolated from CSF cultures (Table 3). Among patients with progressive MS, 80% of patients (16/20) were culture positive (Table 4). One culture-negative MS patient (#3) was taking ofloxacin for a urinary tract infection at the time of CSF culture. *C. pneumoniae* was isolated from CSF in 3 OND control patients (Table 5). One of these three patients (#8) was diagnosed as having post infectious encephalomyelitis (PIE), which may, in fact, represent a variant of MS. The remaining two patients presented with inflammatory myelopathy; one case of unknown etiology and the other case thought to be due to HSV-2. In the latter two patients, changes consistent with inflammatory myelopathy were seen on MRIs of the spinal cords.

The presence of *C. pneumoniae* in the CNS was also evaluated by polymerase chain reaction (PCR) methods which assayed CSF for the major outer membrane protein (MOMP) gene of *C. pneumoniae*. The specific 1.2 kb band for the MOMP gene seen following ethidium bromide staining of agarose gels was confirmed by Southern hybridization using labeled MOMP gene probes (Dalhoff and Maass, Chest 110:351–356, 1996). The MOMP gene for *C. pneumoniae* was amplified and confirmed in all 17 (100%) relapsing remitting MS patients (Table 3) and 19 of 20 (95%) progressive MS patients (Table 4) versus 5 of 27 (18%) OND controls (Table 5). One progressive MS patient (#9) and one OND control (#8) were negative for the MOMP gene, but were positive by culture. Of the five OND control patients who were positive for the MOMP gene, three had thoracic myelitis (#18, #21, #23), the fourth (#1) had acute inflammatory demyelinating polyneuropathy (AIDP), while the fifth (#20) had a stroke. In both groups of relapsing remitting and progressive MS patients, all culture-negative MS patients were positive by PCR/Southern hybridization (PCR/S) assays.

Indirect evidence of *C. pneumoniae* infection in the CNS was determined by the detection of CSF antibodies against preparations of *C. pneumoniae* elementary bodies that had been reduced, solubilized, and sonicated using an ELISA method (Ladany et al., J. Clin. Microbiol. 27:2778–2783, 1989). To ensure that differences in the ELISA absorbance signal were not due to differences in the concentration of antibodies in the CSF, the amount of immunoglobulins in CSF was determined by nephelometric methods in order to add equal amounts to the ELISA plates. Mean absorbance OD values for anti IgG antibody response to EB antigens using CSF from 17 relapsing remitting MS patients was 0.185±0.042 while the mean OD in the control OND group was 0.078±0.025 ($p<0.01$ Fisher's test). Of 17 patients with relapsing remitting MS, 15 patients (88%) had OD values that were three standard deviations from the OND group. The anti IgM response to EB antigens of *C. pneumoniae* expressed as OD units was 0.115±0.02 in the RRMS group and 0.086±0.011 in the OND group ($p<0.05$). When the antibody titers in patients with progressive MS were examined, the mean OD of 20 progressive MS patients was 0.237±0.11, while in the OND control group it was 0.093±0.022 ($p<0.001$ Fisher's test). Seventeen of 20 (85%) MS patients tested had absorbance values in CSF that were three standard deviations greater than those seen in controls. These observations demonstrated that increased CSF antibodies against *C. pneumoniae* were present in the majority of patients with relapsing-remitting and progressive MS.

The specificity of the CSF antibodies was evaluated by Western blot assays using EB antigens (Friedank et al., Eur. J. Microbiol. Infect. Dis. 12:947–951, 1993). Equal amounts of CSF immunoglobulins were incubated with EB antigens in order to control for differences in immunoglobulin concentrations in the CSF. All relapsing remitting MS patients (17/17) showed prominent reactivity to a 75 kD protein of *C. pneumoniae*. In addition, 17 of 20 CSF samples from MS patients demonstrated prominent reactivity to a 75 kD protein of *C. pneumoniae* with weaker reactivity to 65 kD, 60 kD, and 55 kD proteins observed in 13 of these 20 MS patients. In 19 of these 20 MS patients, the strength of the bands seen on Western blot correlated with the ELISA OD units. In contrast, reactivity to this 75 kD protein was seen in only 4 of 20 OND controls. In all 4, the reactivity was weak when compared to MS patients. One of these OND control with PIE (#8) was culture-positive for *C. pneumoniae*. Another patient (#1) with AIDP was positive by PCR/S to *C. pneumoniae* but culture-negative. The other two OND controls (#5 and #17) with positive Western blots were negative for *C. pneumoniae* by culture and PCR/S (Table 5).

The pattern of antibody reactivity on Western blots was similar in all MS patients. The nature of the 75 kD protein band seen in the majority of MS patients as well as in three OND controls is not known. Silver-stained gels of *C. pneumoniae* EB antigens failed to show a dominant band at that molecular weight. Others have reported antibody reactivity to a 75 kD heat shock protein in the serum of patients following *C. pneumoniae* infection (Campbell et al., Infect. Immun. 57:71–75, 1989). When Western blots were performed using cytosolic lysates from uninfected HL cells, no binding of antibody was seen in either the MS patient or the OND group, demonstrating that the antibody binding was specific for elementary body antigens of *C. pneumoniae*.

MS patients are known to have an increase in CSF immunoglobulins in which a portion of this increase is seen as oligoclonal bands on isoelectric focusing gels. These oligoclonal bands represent cationic antibodies that have isoelectric points in the anodic region of the gel. The presence of these cationic antibodies in the CSF was evaluated by isoelectric focusing (IEF) of CSF followed by Western blot assays using EB antigens. Of 20 progressive MS patients, 12 had CSF immunoglobulins at isoelectric points of 7.5 or greater, that reacted with EB antigens. Two OND control patients, one of whom was positive by culture (#8) and the other by PCR/S (#1) demonstrated similar cationic antibodies against EB antigens. These results suggest that cationic anti-chlamydial antibodies are present in the CSF of patients with MS and represents, in part, the specificities for the characteristic oligoclonal bands seen in MS. These and additional findings are described in Example 3, below.

EXAMPLE 2

Detection of the *C. pneumoniae* 16S RNA Gene in the CSF of MS Patients

A) Materials and Methods

Patients and Patient Selection

Seventeen patients with relapsing-remitting MS, six patients with progressive disease (five secondary progressive, one primary progressive) who satisfied the Poser criteria for definite MS, were selected for the study. Age and gender matched controls were recruited from 13 patients with other neurologic diseases (OND) in whom CSF was being obtained for diagnostic studies. In addition, CSF from two patients with subacute sclerosing pan encephalitis were examined in the immunoblot assays.

PCR Amplification of 16S rRNA gene of *C. pneumoniae*

To at least 300 μl of CSF sample in its original collection tube, 200 μl of HBSS containing 0.25% trypsin, 1 mM EDTA at pH 7.2 was added to achieve a final concentration of 0.1% trypsin. The sample was then vortex mixed and incubated at 37° C. for 30 minutes. Following incubation, the sample was again vortex mixed and centrifuged for 45 minutes at 12,000×g in a microcentriflige at ambient temperature. The pellet was resuspended in 20 μl of lysis buffer (0.5% SDS, 1% NP40, 0.2 M NaCl, 10 μM DTT, 10 mM EDTA, and 20 mM Tris-HCl at pH 7.5). Following perturbation of the chlamydial surface by reduction of its extensive disulfide bonding, 8 μl of proteinase K (20 μg/ml) was added. The specimen was mixed and incubated at 37° C. overnight. Purified DNA was then extracted from the aqueous fraction of the specimen with Na acetate (1:10 dilution by volume of a 3 M solution) and mixing/precipitation with 2:2.5 dilution by volume of absolute ethanol at 4° C. after performing initial extraction with a mixture of phenol:chloroform:isoamyl alcohol (25:24:1; Sigma Chemical) followed by two extractions with chloroform. The DNA precipitate was washed with 70% ethanol in water, centrifuged at 600×g for five minutes at ambient temperature, and resuspended in 20 μl of water.

Nested PCR was carried out to detect the 16S rRNA gene of *C. pneumoniae* as follows: The 16S rRNA gene primers used were outer forward (TTT AGT GGC GGA AGG GTT AGT A (SEQ ID NO: 5)), outer reverse (CAC ATA TCT ACG CAT TTC ACC G (SEQ ID NO: 6)), inner forward (CTT TCG GTT GAG GAA GAG TTT ATG C (SEQ ID NO: 7)), and inner reverse (TCC TCT AGA AAG ATA GTT TTA AAT GCT G (SEQ ID NO: 8)). With this nested PCR procedure, the outside 16S rRNA primers amplify members of the Chlamydia genus while the inner 16S rRNA primers are specific for *C. pneumoniae* and amplify a 446 base pair sequence. Reaction mixtures for the outer primer reaction contain 20 μl of target DNA, 200 μM of each outer primer, 200 μM of each dNTP, and 1 unit of Deep Vent polymerase in the manufacturers buffer (New England Biolabs) with no additional MgCl$_2$. The PCR reaction was performed for 35 cycles at 94° C. for 1 minute, 55° C. for 2 minutes, and 74° C. for 3 minutes. Five microliters of the reaction mix is removed from the reaction tube and placed in a second tube containing the same components with the exception that inner primers are used instead of the outer primers. Reaction conditions for the second nested phase were 35 cycles at 94° C. for 1 minute, 50° C. for 2 minutes, and 74° C. for 3 minutes. The reaction products are then subjected to electrophoresis in 1% agarose gels for 45 minutes at 95 V. Amplified DNA was transferred from the agarose gel to positively charged nylon membranes (Boehringer-Mannheim) by capillary blotting. The 16S rRNA gene homologous to the inner primers first was obtained by PCR from the TWAR strain of *C. pneumoniae* (VR-1310, ATCC). This inner primer product was then labeled with DIG following the manufacturers directions. DIG-labeled inner product was used as a probe for membranes prehybridized at 65° C. in hybridization buffer (10% dextran sulfate, 1 M NaCl, 1% SDS) by adding 100 ng of DIG-labeled probe in fresh hybridization buffer and incubated overnight at 65° C. overnight. Blots were washed three times in 2×saline-sodium citrate containing 1% SDS at ambient temperature and an additional three times at 65° C. followed by high stringency washes in 0.1×saline-sodium citrate containing 0.1% SDS at ambient temperature. Membranes were blocked in 5% w/v dehydrated nonfat milk in PBS, 0.2% Tween 20 for one hour at ambient temperature, then incubated in anti-DIG-alkaline phosphatase-conjugated Fab fragments (Boehringer-Mannheim) diluted 1:5000 in PBS, 0.2% Tween 20, and developed with NBT/BCIP substrate.

B) Results

Presence of 16S rRNA in CSF Correlates With MS

Figure 1:
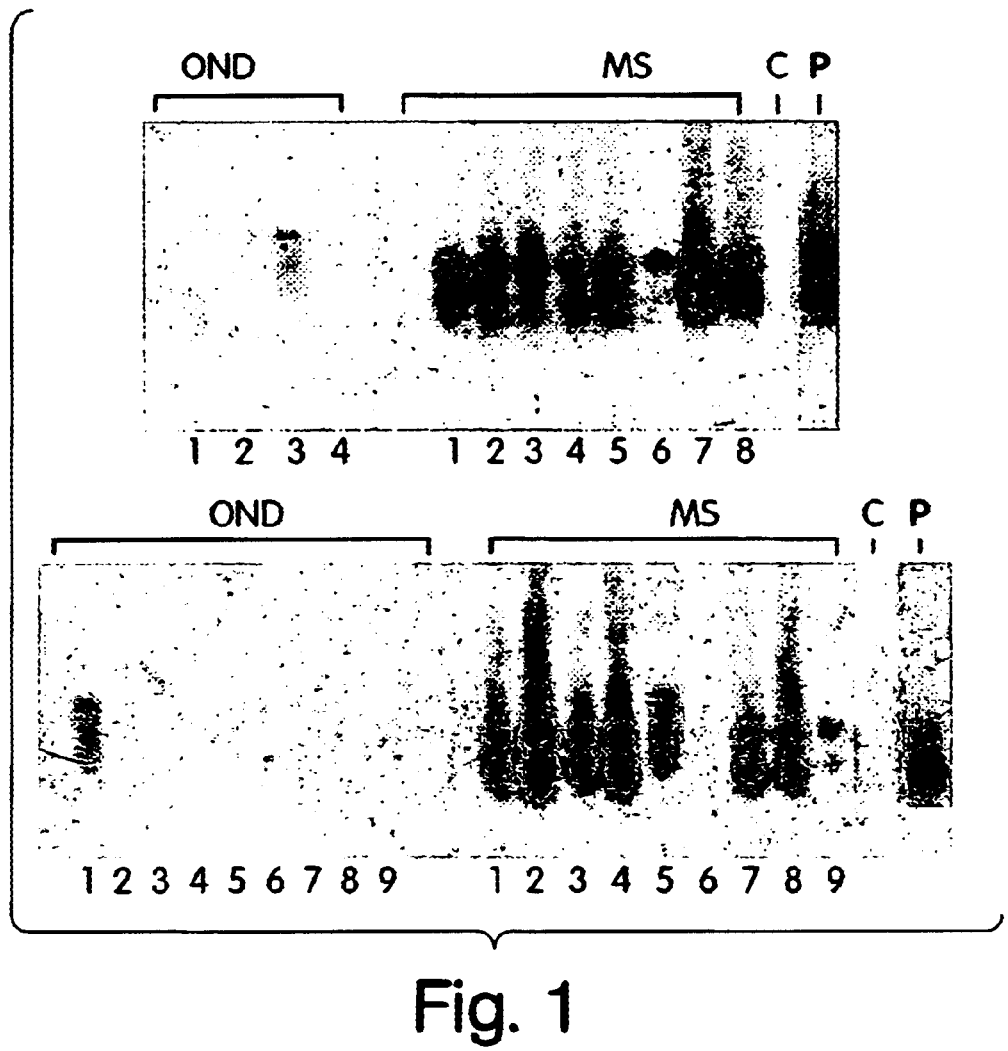
FIG. 1 is a schematic illustration showing visualization of a 446 base pair region of the 16S rRNA gene of *Chlamydia pneumoniae* (also referred to as *Chlamydophila pneumoniae*) amplified by a nested PCR procedure and followed by Southern hybridization with a digoxigenin-labeled specific probe. The gels represent cerebrospinal fluid (CSF) from 17 patients with relapsing remitting MS and 13 patients with other neurological diseases (OND) controls. The gels include quality control markers. Lane P represents a positive control of *C. pneumoniae* (VR1310, American Type Culture Collection (ATCC); Manassas, Va.) while lane C represents a distilled water negative control that has been subjected to the entire PCR procedure.
Figure 2:
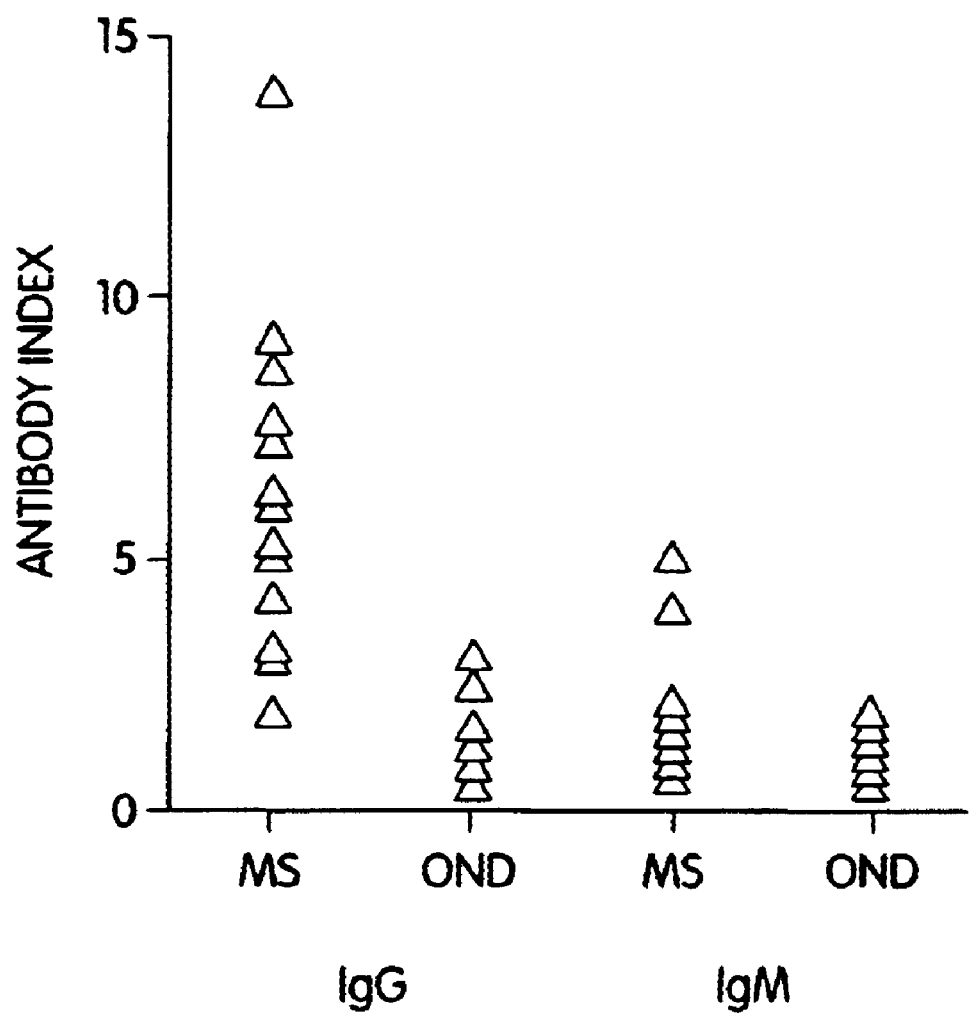
FIG. 2 is a schematic illustration showing ELISA results of anti-IgG and anti-IgM antibodies in CSF to elementary body (EB) antigens of *C. pneumoniae* in MS patients and controls. Antibody index is represented as the ratio of OD units measured by ELISA in patient group over OD units of CSF from five pooled normal CSF samples to EB antigens of *C. pneumoniae*. In all experiments, 1 μg of immunoglobulin was added to microtiter wells.
Figure 3A:
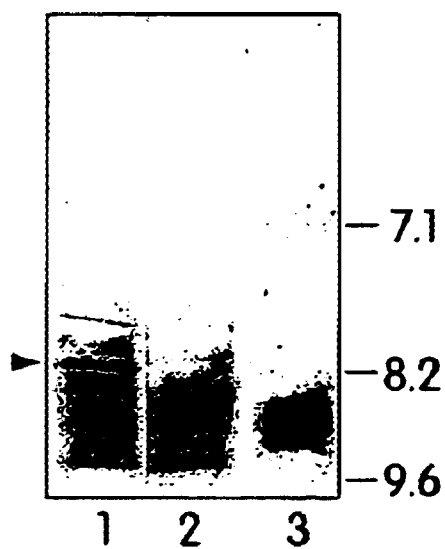
FIGS. 3A–3D are a series of schematic illustrations showing affinity-driven immunoblot studies on four MS patients. In each figure, lanes 1–4 represent the banding pattern of oligoclonal antibodies following affinity-driven transfer onto untreated (lane 1), *C. pneumoniae* antigen-coated (lane 2), measles-antigen coated (lane 3), or HSV-1 antigen-coated (lane 4) nitrocellulose membranes and probed with anti-human Ig antibody.
Figure 3B:
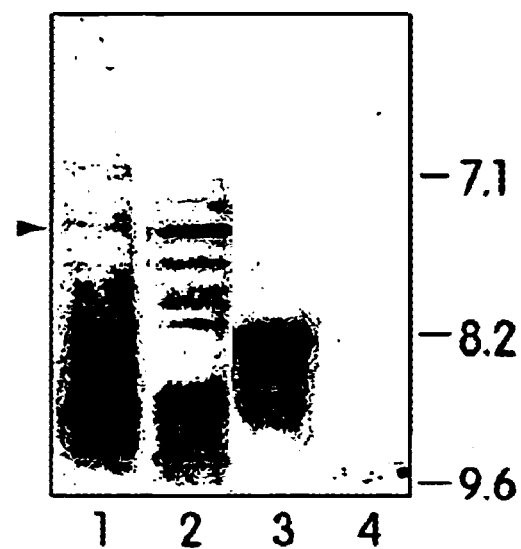
Figure 3C:
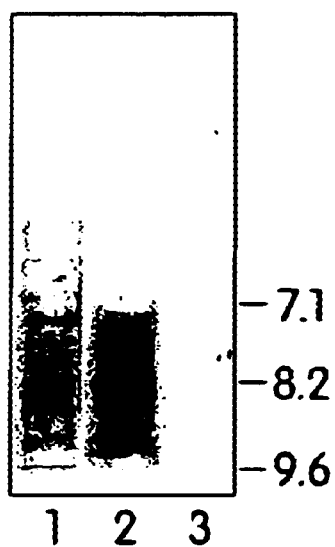
Figure 3D:
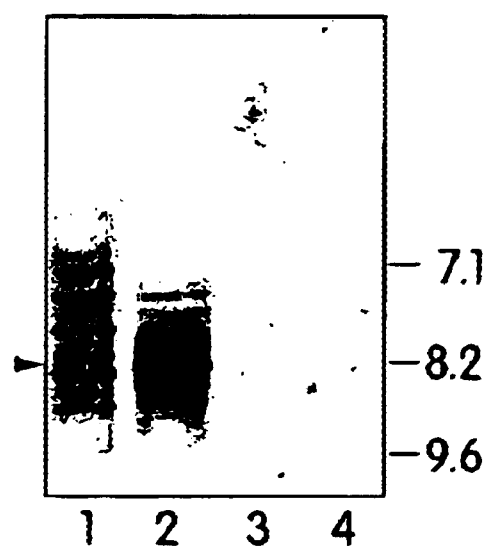
Figure 4A:
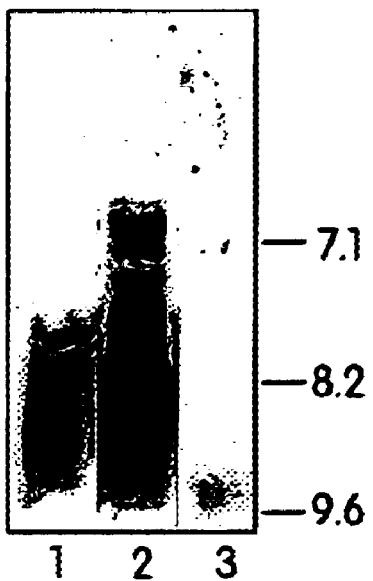
FIGS. 4A–4D are a series of schematic illustrations showing affinity-driven immunoblot studies on four OND patients.
Figure 4B:
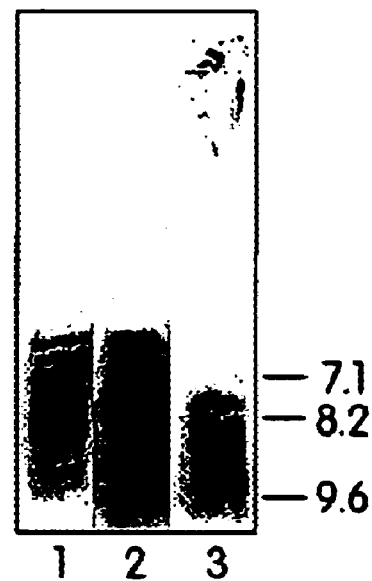
Figure 4C:
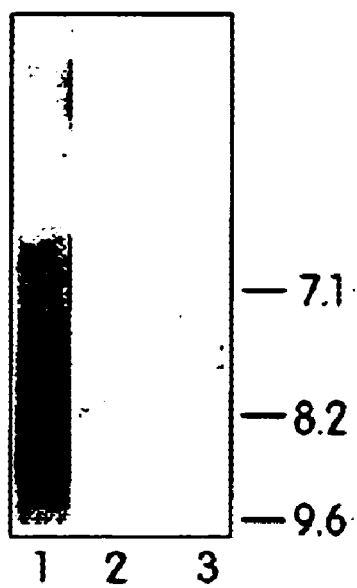
Figure 4D:
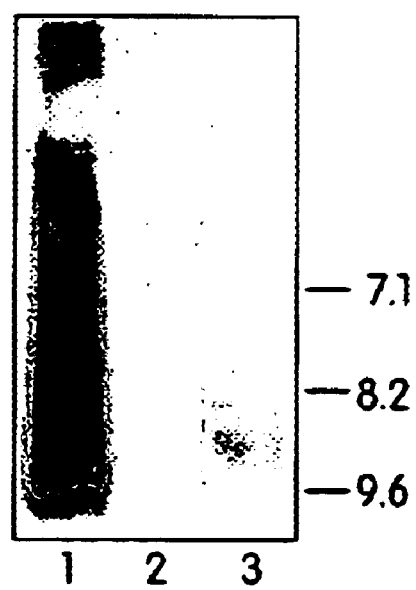
Figure 5A:
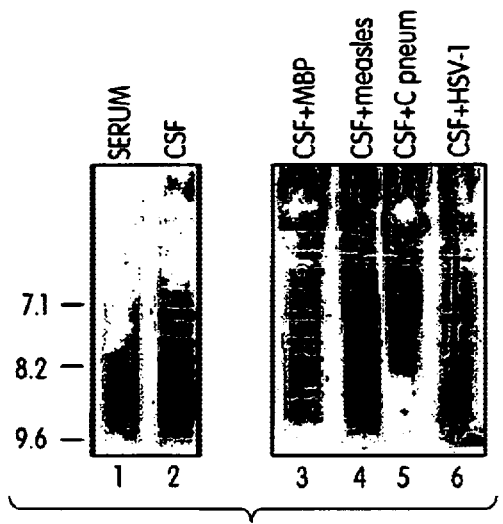
FIGS. 5A–5J are a series of schematic illustrations showing adsorption studies on CSF immunoglobulins to EB antigens of *C. pneumoniae*, measles, HSV-1, and MBP for 10 patients with progressive MS. For each individual patient, the left two lanes represent IEF gel patterns for 0.8 μg Ig of unmanipulated serum and CSF, respectively, while the right lanes represent the IEF gel patterns following incubation with antigens as labeled.
Figure 5B:
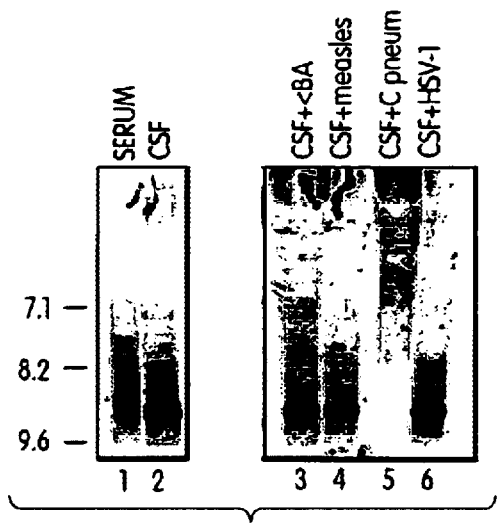
Figure 5C:
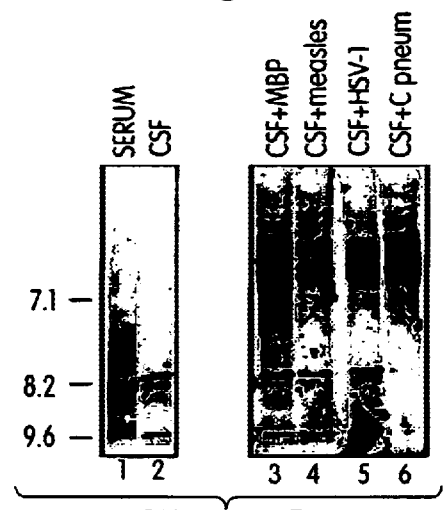
Figure 5D:
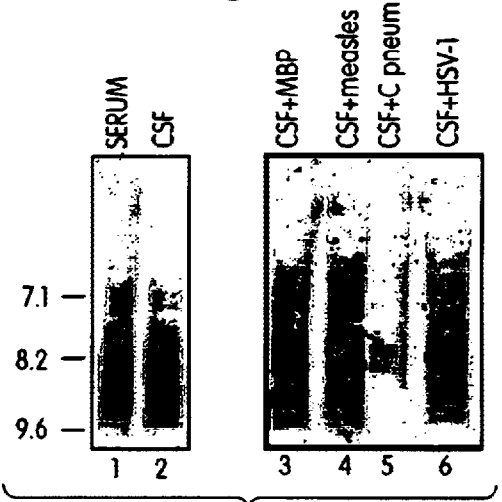
Figure 5E:
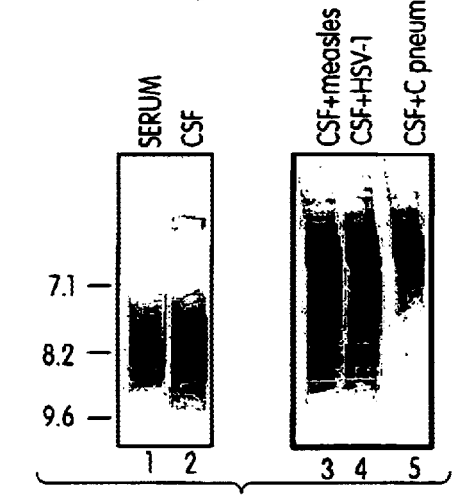
Figure 5F:
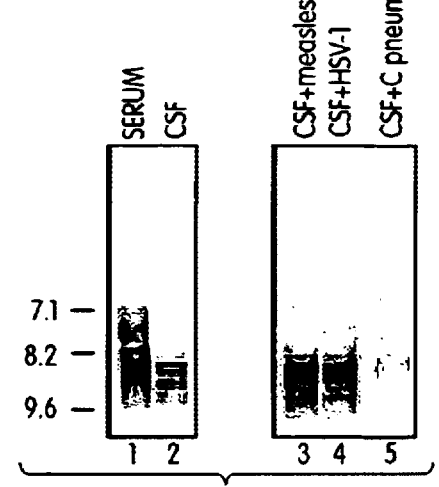
Figure 5G:
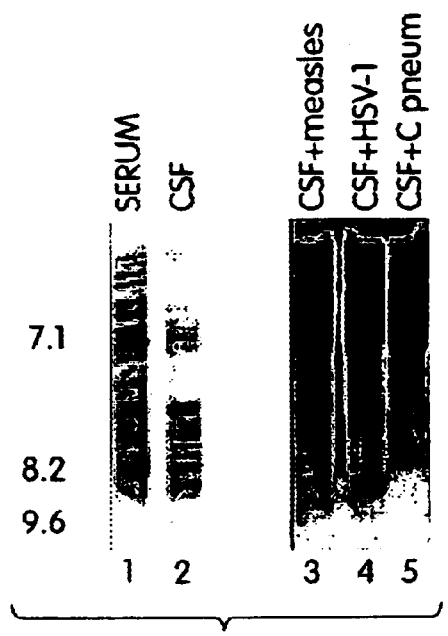
Figure 5H:
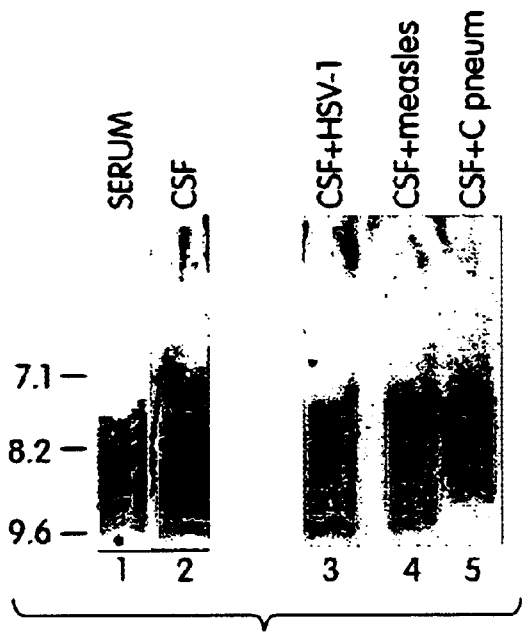
Figure 5I:
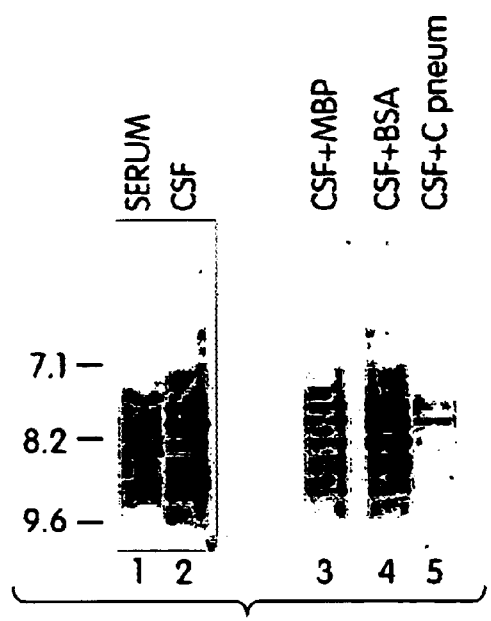
Figure 5J:
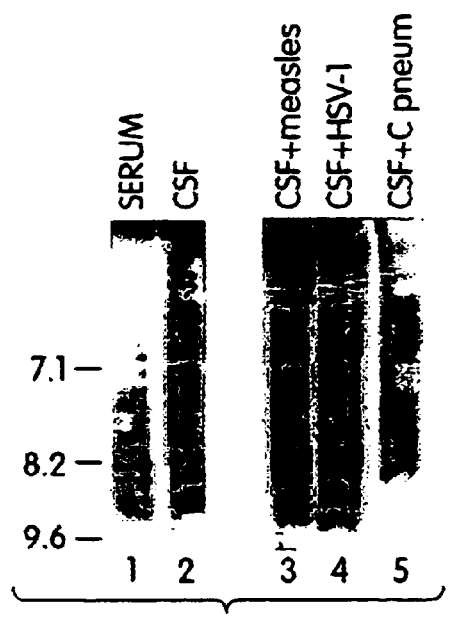

Fifteen of 17 (88%) of the CSF samples from MS patients contained DNA specific for the 16S rRNA gene of *C. pneumoniae* (FIG. 1). Of these 15 CSF samples that were positive by PCR, 8 yielded strongly positive signals for the 446 base pair *C. pneumoniae* product. Because the 643 base pair outer primer product also was present in the sample used in the nested PCR, labeling of it was seen as would be expected. One of the CSF samples from MS patients read as negative (number 5, lower gel) contained hybridization-specific products with a significantly higher size of the major band. This may represent a Chlamydia with a mutation within the inner primers yielding a product of approximately 520 base pairs. In contrast, only two of the 13 CSF samples from the OND control group (number 3, upper gel and number 1, lower gel) yielded some weak hybridization product of the incorrect base pair size and were scored as PCR negative.

EXAMPLE 3

Cationic Anti-Chlamydial Antibodies in the CS F of Patients With MS

To further demonstrate that *C. pneumoniae* infection is causal to the development of MS, we analyzed the specificity of the intrathecal humoral response and, in particular, the reactivity of the oligoclonal bands from patients with relapsing remitting and progressive MS against *C. pneumoniae* antigens. In virtually every chronic infection of the CNS, increased levels of immunoglobulins that recognize the pathogen are synthesized exclusively within the CNS compartment and are seen as oligoclonal bands by IEF methods. In MS, oligoclonal bands are a hallmark of the disease, although the antigenic specificity of these bands has been unknown. Described below are experiments that examine the pattern and specificity of reactivity of oligoclonal bands (representing intrathecal antibody synthesis) to *C. pneumoniae*, MBP, measles, and HSV-1 antigens in MS patients and OND controls.

A) Materials and Methods

Patients and Patient Selection

Patients who satisfied the criteria of definite MS were recruited for the present study. In all, 15 MS patients (eight secondary progressive, two primary progressive, five relapsing remitting) were studied. Age and gender matched OND patients in whom CSF was being obtained for diagnostic studies, served as controls and have also been described previously. In all patients, CSF and, when possible, serum was aliquoted into 0.5 ml freezing vials and stored at −70° C. before use. CSF samples from patients with subacute sclerosing pan-encephalitis (SSPE) were a kind gift of Dr. ter Muelen (Freiberg, Germany). Dr. S. Jacobson (NIH, Bethesda, Md.) kindly provided CSF samples from patients with HTLV-1 myelopathy.

Preparation of Purified EBs of *C. pneumoniae*

EB antigens of *C. pneumoniae* were prepared from concentrated EBs by treating them with 25 mM DTT and 2% 2-mercaptoethanol for 5 minutes at 100° C. EBs were then sonicated and centrifuged (500×g for 30 minutes at room temperature). EB antigens were resuspended (20 μg/ml protein) in PBS pH 7.4 and used for all experiments.

Concentrated *C. pneumoniae* EBs were obtained by growing *C. pneumoniae* (VR-1310; ATCC) in the HL cell line. EBs were harvested and resolubilized in Iscoves minimal essential medium and their purity assessed by SDS-PAGE electrophoresis followed by Western blotting with anti-*C. pneumoniae* antibody (Accurate Chemical & Scientific Corp, Westbury, N.Y.)

Measurement of Antibody Levels in CSF to EB Antigens of *C. pneumoniae* by ELISA Microtiter 96-well plates were coated with EB antigens of *C. pneumoniae* (1 μg/well). Plates were incubated overnight and unoccupied sites blocked with 1% BSA/PBS-Tween 20 for one hour. The CSF samples were added to each well in a final concentration of 1 μg of immunoglobulin diluted in 100 μl of PBS as determined by nephelometric methods and incubated overnight at 4° C. Following this step, the plates were washed with PBS-Tween 20, and then peroxidase-conjugated goat anti-human IgG (1:10,000) (Sigma Chemical Co.) was added. Following two hours of incubation, the plates were washed with PBS-Tween 20 and the substrate added. The absorbance at 405 nm was read using an ELISA reader (BioTech Instruments, Burlington, Vt.) at one hour. CSF from five patients in whom all CSF studies were normal was pooled and served as an internal control. This pooled CSF was used to determine basal optical density units to EB antigens in the ELISA. Antibody titers to *C. pneumoniae* EBs were represented as an antibody index, defined as the ratio of absorbance in OD units for the test patient divided by OD units of the control group.

Affinity-Driven Immunoblot Technique for Detection of Antigenic Specificity of Oligoclonal Bands To determine the antigenic specificity of antibodies in CSF, we performed isoelectric focusing of CSF immunoglobulins, followed by affinity-driven transfer of antibodies onto antigen-coated membranes with 0.25 μg of immunoglobulin from CSF obtained from MS patients and OND controls using an Isoelectric Focus Units System (Wallac Inc, Akron, Ohio). Focusing was carried out in agarose gel (pH 3.0–10.0) according to the manufacturer's protocol. Capillary transfer was used to transfer the IEF gel to nitrocellulose paper (Trans-blot, 0.45 μm; Bio-Rad, San Francisco, Calif.) that was pre-coated with antigen. The membrane was pre-coated with *C. pneumoniae* EB or viral antigens at a concentration of 5 μg/ml and incubated overnight with gentle rocking at 4° C. Control antigens for blotting experiments were measles, HSV-1 (Bio-Whittaker, Inc, Walkersville, Md.), and guinea pig MBP. Unoccupied sites were blocked with 5% fat-free milk. Antibody bound to antigen was probed with peroxidase-conjugated goat anti-human IgG (1:10,000) (Sigma) using a chemiluminescent detection assay.

Solid Phase Adsorption of Cationic Antibodies in CSF to *C. pneumoniae*

Purified EBs of *C. pneumoniae* were heated to 100° C. for five minutes, sonicated for 30 seconds, resuspended in carbonate buffer, pH 9.6, and coated (20 μg/well) overnight onto microtiter 96 well plates. The wells were washed in PBS and unoccupied sites blocked using 1% BSA for two hours. CSF samples containing 0.8 μg of Ig in 200 μl of saline (pH 7.4) were added to the 96 well plates. Control antigens (20 μg/well) to which CSF Ig samples also were incubated included MBP, measles, and HSV-1. After overnight incubation at 4° C., CSF containing unbound Ig was carefully removed and lyophilized. Immunoglobulins were redissolved in 30 μl of water immediately prior to running an IEF gel. Samples containing 0.25 μg of Ig (10 μl) were loaded into an IEF gel, and isoelectric focusing was performed. The gel was transferred onto nitrocellulose membranes, and the presence of Ig bound to antigen on the membranes was probed with peroxidase-conjugated goat anti-human IgG (Sigma) using a chemiluminescence detection assay (Amersham, Arlington Heights, Ill.).

B) Results

Measurement of Antibodies (IgG and IgM) in CSF of MS Patients and OND Controls Against EB Antigens of *C. pneumoniae* by ELISA Methodology Antibody titers to *C. pneumoniae* were measured using ELISA methodology for 10 patients with progressive (secondary and primary) MS, five patients with relapsing remitting MS, and 14 OND controls. The mean anti-IgG antibody index to *C. pneumoniae* antigens in the 15 MS patients was 6.1±2.9 ($p<0.001$ versus OND control; FIG. 1). In all but three MS patients, the antibody index was at least three standard deviations greater than that seen in controls. The mean antibody index in the 12 OND control patients was 1.3±0.8. In the two SSPE patients, the antibody index was 2.5 and 2.6, while in the remaining 10 OND patients, the antibody index ranged between 0.5 and 2.2. The mean anti-IgM antibody indices to *C. pneumoniae* in MS patients and controls were not statistically different (antibody index for MS was 2.0±1.6, OND 1.3±0.5). These results reflect the persistence of the intrathecal humoral immune response to *C. pneumoniae* in MS patients over that of OND controls.

Affinity-Driven Immunoblots for Antigen Specificity of Oligoclonal Bands in MS Patients and OND Controls In all 15 MS patients, cationic antibodies (seen as oligoclonal bands) showed binding to *C. pneumoniae* antigens following affinity-driven immunoblot transfer (Table 6). Representative patterns of the immunoblots following transfer onto antigen-coated membranes are shown in FIG. 2 (four MS patients) and FIGS. 3A–3D (four OND controls). In all MS patients, the binding of *C. pneumoniae* antigens to the cathodal antibodies closely reflected the CSF immunoglobulin pattern seen on IEF gels transferred onto non-antigen-coated membranes. The prominence of the signal of individual oligoclonal bands following transfer onto EB-coated membranes differed in intensity, although not in their overall pattern, suggesting differences in the affinity of the individual oligoclonal bands to the antigen. When reactivity to other antigens were examined, weak binding to measles antigen was seen in nine of 15 patients (see, for example, FIG. 3A and Table 6). None of these bands matched patterns to that seen following transfer of immunoglobulin to *C. pneumoniae*-coated membranes. Representative patterns of four affinity-driven immunoblots for OND controls are shown in FIGS. 4A–4D. In two SSPE patients, as expected, oligoclonal bands seen on IEF gels were bound to measles antigen following transfer. In patient #2 (Table 7), reactivity of some of the cathodal antibodies to *C. pneumoniae* antigens was seen. Weak binding to *C. pneumoniae* antigens was also seen for patient #9 (Table 7), who presented with clinical features of HSV-2 myelitis. This patient was positive in the CSF by PCR and culture for *C. pneumoniae*. This patient has now presented with a second lesion in the thoracic cord and fulfills the clinical criteria for relapsing remitting MS.

TABLE 6

| Patient | Age/Sex | EDSS Scale | IgG | Oligoclonal Bands | ELISA IgG | ELISA IgM | Immunoblot Measles | Immunoblot HSV-1 | Immunoblot C. pneumoniae | Adsorption EB Ag | Adsorption Measles |
|---|---|---|---|---|---|---|---|---|---|---|---|
| 1 | 40/M | 6.5 | 0.64 | Positive | 4.2 | 1.89 | Positive | Negative | Positive | Yes/Partial | No |
| 2 | 54/M | 8.5 | 1.38 | Positive | 14.0 | 2.0 | Weak Positive | Negative | Positive | Yes | ND |
| 3 | 42/F | 6.5 | 1.73 | Positive | 6.2 | 5.0 | Positive | Positive | Positive | Yes | No |
| 4 | 36/F | 8.0 | NA | Positive | 6.2 | 2.2 | Negative | Negative | Positive | Yes | No |
| 5 | 35/F | 7.5 | 3.69 | Positive | 9.25 | 1.6 | Positive | Positive | Positive | Yes | No |
| 6 | 29/M | 3.0 | 1.2 | Positive | 6.0 | 0.7 | Positive | Negative | Positive | Yes | No |
| 7 | 28/M | 3.5 | 2.3 | Positive | 7.25 | 1.55 | Negative | Positive | Positive | Yes/Partial | No |
| 8 | 55/M | 8.5 | NA | Positive | 8.6 | 1.4 | Positive | Negative | Positive | Yes | No |
| 9 | 51/M | 7.0 | 0.49 | Positive | 3.0 | 1.5 | Positive | Negative | Positive | Yes | ND |
| 10 | 46/F | 7.0 | 0.9 | Positive | 7.6 | ND | Negative | Negative | Positive | No | No |
| 11 | 44/M | 3.5 | 0.67 | Positive | 3.2 | 1.6 | Negative | ND | Positive | No | No |
| 12 | 20/F | 1.0 | 1.4 | Positive | 2.0 | 1.1 | Positive | ND | Positive | Yes | No |
| 13 | 24/F | 6.5 | 0.9 | Positive | 5.2 | 1.5 | Negative | ND | Positive | Yes | No |
| 14 | 49/M | 1.5 | 1.19 | Positive | 5.0 | 2.0 | Negative | ND | Positive | Yes/Partial | No |
| 15 | 26/F | 3.0 | 1.09 | Positive | 5.7 | 4.2 | Positive | ND | Positive | Yes | No |

TABLE 7

| Patient | Age/Sex | Diagnosis | Oligoclonal Bands | ELISA IgG | ELISA IgM | Immunoblot Measles | Immunoblot C. pneumoniae | Absorption C. pneumoniae | Absorption Measles |
|---|---|---|---|---|---|---|---|---|---|
| 1 | NA | SSPE | Positive | 2.6 | 1.5 | Positive | Negative | No | Yes |
| 2 | NA | SSPE | Positive | 2.5 | 1.2 | Positive | Positive | No | Yes |
| 3 | NA | SSPE | Positive | ND | ND | Positive | Negative | No | Yes |
| 4 | 32/M | Vasculitis | Negative | 1.7 | 2.0 | Positive | Negative | ND | ND |
| 5 | 36/F | CNS Lupus | Negative | 0.9 | 0.5 | Positive | Negative | No | ND |
| 6 | 26/M | Meningitis | Positive | 0.5 | 1.1 | Negative | Negative | No | No |
| 7 | 52/M | CNS Syphilis | Positive | 1.35 | 2.0 | Positive | Negative | No | No |
| 8 | 38/F | HSV-2 Myelitis | Negative | ND | ND | Positive | Negative | ND | ND |
| 9 | 28/F | HSV-2 Myelitis | Negative | 1.25 | 1.5 | Negative | Weak Positive | No | No |
| 10 | 36/M | CNS Sarcoid | Negative | 0.75 | 0.9 | Negative | Negative | No | No |
| 11 | 69/F | Vasculitis | Negative | 1.56 | 1.5 | Positive | Negative | ND | ND |
| 12 | NA | HTLV-1 Myelitis | NA | 0.95 | 2.09 | Negative | Negative | No | No |
| 13 | NA | HTLV-1 Myelitis | NA | 2.25 | 1.47 | Negative | Negative | ND | ND |
| 14 | NA | HTLV-1 Myelitis | NA | 1.66 | 1.86 | Negative | Negative | ND | ND |

Solid Phase Adsorption of Oligoclonal Bands With EB Antigens of C. pneumoniae

Figure 6D:
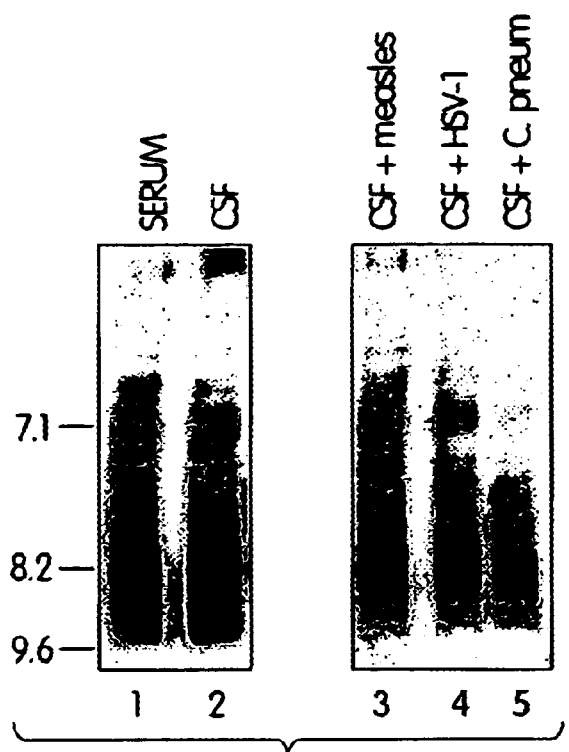
Figure 6E:
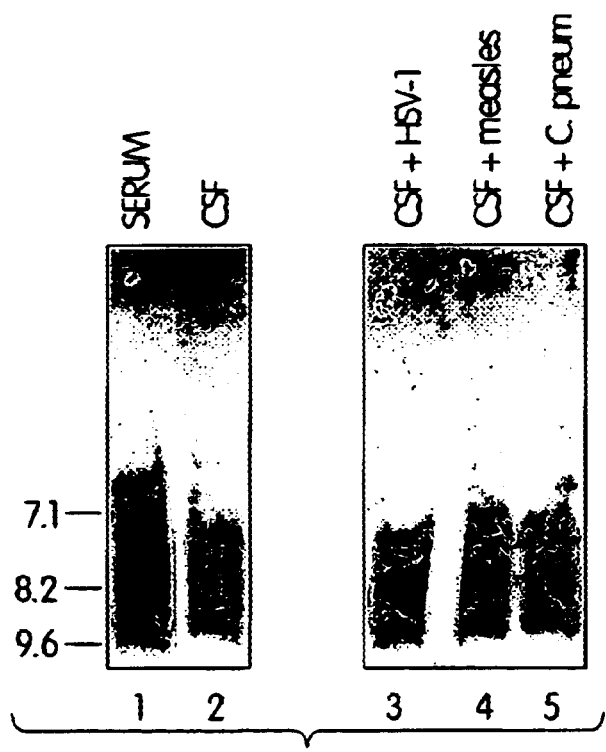
Figure 7A:
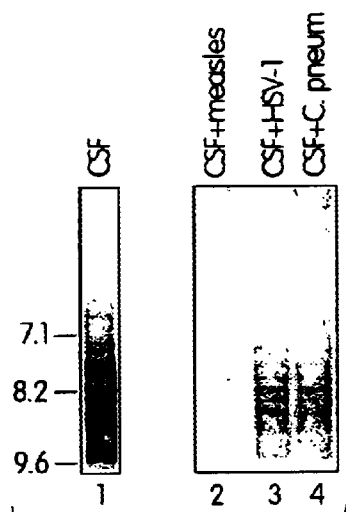
FIGS. 7A–7F are a series of schematic illustrations showing IEF gel patterns following adsorption studies on CSF immunoglobulins for SSPE (FIGS. 7A–7C), CNS syphilis (FIG. 7D), CNS vasculitis (FIG. 7E), and chronic meningitis (FIG. 7F).
Figure 7B:
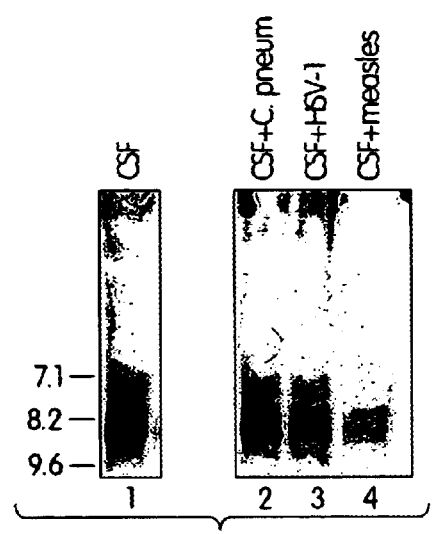
Figure 7C:
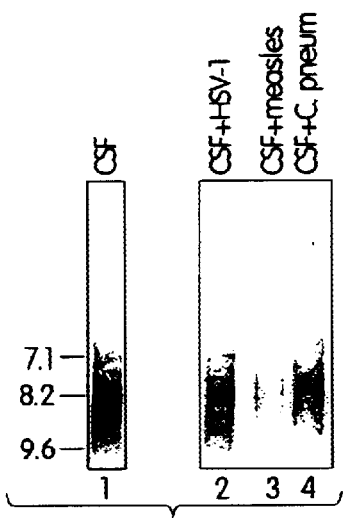
Figure 7D:
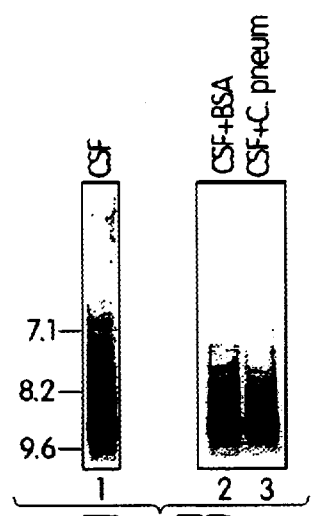
Figure 7E:
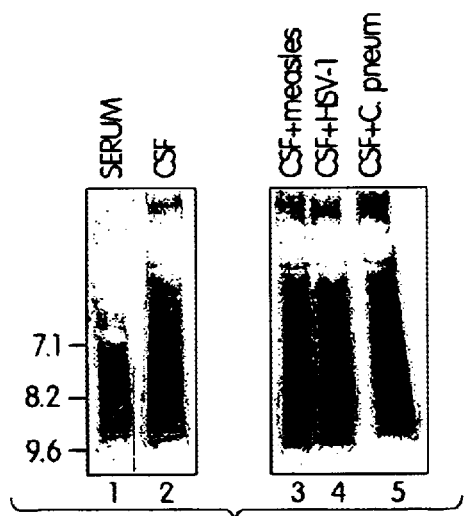
Figure 7F:
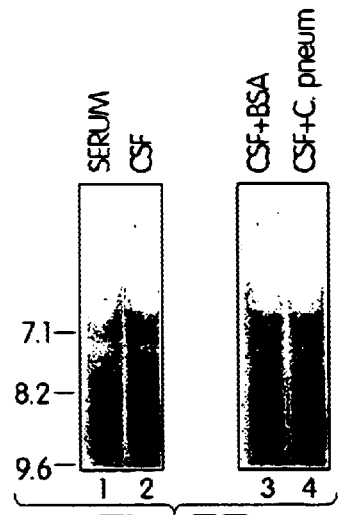

If oligoclonal bands represent the dominant CNS humoral response to C. pneumoniae infection, we predicted the adsorption of these bands by antigens of C. pneumoniae. Adsorption was carried out in solid phase with a 25-fold excess of antigen over antibody (0.8 µg of CSF IgG plated onto microtiter wells incubated with 20 µg/well of antigen). In parallel experiments, CSF samples containing 0.8 µg of IgG were added to wells coated with 25-fold excess of MBP, measles, or HSV-1 antigens, which served as antigen specificity controls. In 10 MS patients, the adsorption by C. pneumoniae EB antigens was complete as no oligoclonal bands were seen at isoelectric points greater than 7.5 (FIGS. 5A–5J). In three of the remaining five MS patients, adsorption of oligoclonal bands with C. pneumoniae was incomplete (FIGS. 6A–6C), while, in two, no clear evidence of adsorption was seen (FIGS. 6D and 6E; Table 6, patients #10 and 11).

Nine patients in the OND group were studied; representative patterns of six are shown in FIGS. 7A–7F. No changes in the chemiluminescence signal of the oligoclonal bands were seen following adsorption with C. pneumoniae antigens in eight of nine patients. Oligoclonal bands were adsorbed with excess measles antigen in all three SSPE patients, but not with HSV-1 or EB antigens, suggesting that the anti-measles antibody response in the CSF constituted the major antibody response in SSPE patients. In patient #2 (Table 7), cathodal antibodies reactive to EB antigens of C. pneumoniae were seen on affinity-driven immunoblots (FIGS. 3A–3D). Incubation of CSF from SSPE-2 with EB antigens of C. pneumoniae did not alter the IEF gel, suggesting that the anti-C. pneumoniae antibodies did not comprise the major antibody response in the CSF. In the remaining five patients with inflammatory disease of the CNS, no difference in the banding pattern of cathodal antibodies was seen following adsorption with EB antigens of C. pneumoniae. These results suggest that the majority of oligoclonal bands in CSF of MS patients represent antibodies to C. pneumoniae antigens. Non-specific adsorption of antibodies to C. pneumoniae antigens in MS patients was an unlikely explanation, since antibodies present in the anodal region did not bind to C. pneumoniae antigens. Also, no decrease in the oligoclonal bands was seen among nine OND controls following incubation with C. pneumoniae antigens.

EXAMPLE 4

Beta Interferon Enhances Intracellular Nitric Oxide Activity and Inhibits Secretion of Interleukin-12/p40

A) Materials and Methods

Mice and Reagents

Female SJL/J mice from Clarence Reader (National Institutes of Health, Bethesda, Md.) were maintained in the animal care facility at Vanderbilt University Medical Center. Murine β-IFN and sheep anti-mouse-β-IFN antibodies were obtained commercially (Bio-Source International, Camarillo Calif.). Control sheep immunoglobulin and LPS were obtained from Sigma Chemical (St. Louis, Mo.). Monoclonal rat anti-murine IL-12 hybridomas C17.15 and C15.8 were supplied by G. Trinchieri (Wistar Institute, Philadelphia, Pa.), and the respective antibodies were purified from ascitic fluid from nude mice.

Preparation and Stimulation of Splenic Macrophages

Splenocytes were washed twice in PBS and plated in 24-well culture plates (Corning, Corning, N.Y.) in Dulbecco's minimal essential medium (DMEM; GIBCO BRL, Gaithersburg, Md.) containing 10% fetal calf serum (FCS; Hyclone, Logan, Utah) at 37° C. for two hours. Non-adherent cells were washed away by gentle rinsing in warm medium, and the macrophages were allowed to adhere to the plastic wells overnight. For optimal growth of macrophages, colony stimulating factor-1 (CSF-1) obtained from culture supernatants of LADMAC cells (American Type Tissue Collection (ATCC), Manassas, Va.) was added to reach a final concentration of 20%. After reaching confluence, cells were removed from the plastic wells by gentle trituration and examined for their purity by staining with fluoroscein-conjugated anti-CD11b and anti-I-As (clone 10-3.6) antibodies. These studies indicated that greater than 90% of cells expressed the macrophage phenotype.

Preparation of EB Antigens

EB antigens were prepared from concentrated *C. pneumoniae* EBs by treating them with 25 mM DTT, 2% 2-mercaptoethanol, and 2% dodecylsulfate (SDS) for 5 minutes at 100° C. Treated EBs were sonicated, centrifuged (500×g for 30 minutes at room temperature) and the supernatant resuspended at 2 µg/ml protein in PBS pH 7.4. Concentrated *C. pneumoniae* EBs were obtained by growing *C. pneumoniae* (VR-1310; ATTC) in 25 ml flasks containing a confluent growth of HL cells (Human Lung Carcinoma Cells; Washington University Foundation, Seattle, Wash.) in DMEM and 10% FCS. Infection was facilitated by two washes with Hank's balanced salt solution (HBSS; GIBCO) followed by a 20 minute pre-incubation with diethylaminoethyl-dextran (30 μg/ml) (DEAE-Dextran; GIBCO) in HBSS. The infectious inoculum (ATCC VR-1310) was added to the flasks in 2 ml of serum-free media. The flasks were then centrifuged at 1,200×g for 1 hour at 4° C. To the spun flasks was added 2 ml of Iscoves medium (GIBCO) containing 4 μg/ml cyclohexamide, 20% FCS, 4 mM L-glutamine (Sigma), and 100 μg/ml gentamicin (Sigma). The flasks were then incubated at 35° C. for three days at which time the infected cells begin to lyse and release EBs. On day 4, the culture flasks were sonicated for 20 seconds, and the cell debris removed by centrifugation at 600×g for five minutes at room temperature. The supernatant containing the infectious EBs was centrifuged at 18,000×g for 30 minutes, and the pellet resolubilized in water containing 25 mM DTT, 2% 2-mercaptoethanol, and 2% SDS.

Preparation of Purified rMOMP

Preparation of purified rMOMP was performed as follows. The full-length native *C. pneumoniae* MOMP gene was expressed in the pET-32/a (+) *E. coli* expression system using a polyhistidine tag (Novagen, Madison, Wis.). Briefly the MOMP was amplified under the same PCR conditions with a NcoI extension on the forward primer and a NotI extension on the reverse primer. The 5' to 3' sequence of the forward primer was AGC TTA CCA TGG TGA ATG AAA AAA CTC TTA AAG TCG GCG (SEQ ID NO: 9) and the reverse primer was ATA TGC GGC CGC TCA TTA GAA TCT GAA CTG ACC AGA TAC G (SEQ ID NO: 10). The product was cut with NotI and NcoI and ligated into the multiple cloning site in a previously linearized pET vector. *E. coli* was transformed and selectively grown, lysed with a French press, and the protein extract was run over a Ni-chelate column and eluted with polyhistidine. Purified rMOMP was isolated by molecular sieve chromatography following cleavage of the tag sequence with thrombin. The purified *C. pneumoniae* rMOMP containing the wild-type sequence was used in the in vitro experiments.

ELISA for IL-12/p40

IL-12/p40 in culture supernatants was quantitated using sandwich ELISA methodology. Antibody C17.15 was coated onto ELISA plates at 2 μg/ml in 100 μl of carbonate buffer at pH 9.3. After overnight incubation at 4° C., excess antibody was washed off, and the plates were blocked by addition of PBS containing 3% BSA. Samples and standards were plated in triplicate and incubated overnight at 4° C. Plates were washed again with PBS containing 0.05% Tween 20 and biotinylated anti-IL-12 antibody (C15.8) antibody was added at 2 μg/ml. After one hour at room temperature, the plates were washed three times with PBS, and avidin-alkaline phosphatase was added followed by the addition of 1 mg/ml p-nitrophenyl phosphate. The absorbance was read at 405 nm and sample concentrations of IL-12/p40 were calculated from a rIL-12/p40 standard curve.

Measurement of NO Production

NO is rapidly oxidized to nitrite in culture medium. Determination of nitrite concentration, therefore, is used as a measurement of NO production. This was done by mixing 50 μl of culture supernatant with 50 μl of Greiss reagent (1% sulfanilamide, 0.1% naphthylethylene diamine dihydrochloride, 2.5% $H_3PO_4$) in individual wells of 96-well tissue culture plates (Corning). After a 10 minute incubation at room temperature, the absorbance was read at 550 nm. Nitrite concentrations were calculated from a sodium nitrite standard curve.

PCR for iNOS

Mouse splenic macrophages were homogenized in TRI reagent (Molecular Research Center, Cincinnati, Ohio), and total RNA was extracted according to the manufacturer's protocol. One microgram of total RNA was reverse transcribed into cDNA in a 20 μl reaction mixture containing 50 U murine leukemia virus reverse transcriptase (MuLV RT), 20 U RNase inhibitor, 1 nM of each dNTP, 2.5 μM random hexamers, 5 mM $MgCl_2$, and 1×buffer containing 50 mM KCl and 10 mM Tris-HCl, pH 8.3 (all reagents from Perkin Elmer) using a gene amplification kit (Perkin Elmer Corp., Norwalk, Conn.). PCR amplification was carried out using 5 μl cDNA in a 25 μl reaction mixture containing 0.625 U AmpliTaq, 12.5 pmol of each primer, 2 mM $MgCl_2$, and 1×buffer (Perkin Elmer). Primers used were as follows:

| | | |
|---|---|---|
| iNOS sense: | 5'-TAG AGG AAC ATC TGG CCA GG-3' | (SEQ ID NO: 11) |
| iNOS antisense: | 5'-TGG CAG CAT CCC CTC TGA TG-3' | (SEQ ID NO: 12) |

-continued

| | | |
|---|---|---|
| GAPDH sense: | 5'-TGA AGG TCG GTG TGA ACG GAT TTG GC-3' | (SEQ ID NO: 13) |
| GAPDH antisense: | 5'-CAT GTA GGC CAT GAG GTC CAC CAC-3' | (SEQ ID NO: 14) |

The PCR reaction was carried out in a PTC-200 programmable thermocycler (MJ Instruments Inc., Waltham, Mass.) for 30 cycles as follows: iNOS, 94° C. for 30 seconds, 56° C. for 1 minute, and 74° C. for 1 minute, with a final extension for 7 minutes; GAPDH, 94° C. for 15 seconds, 55° C. for 20 seconds, and 72° C. for 1 minute. Finally, 7 µl of the PCR product was run on a 1% agarose gel in TAE buffer.

B) Results

Figure 8A:
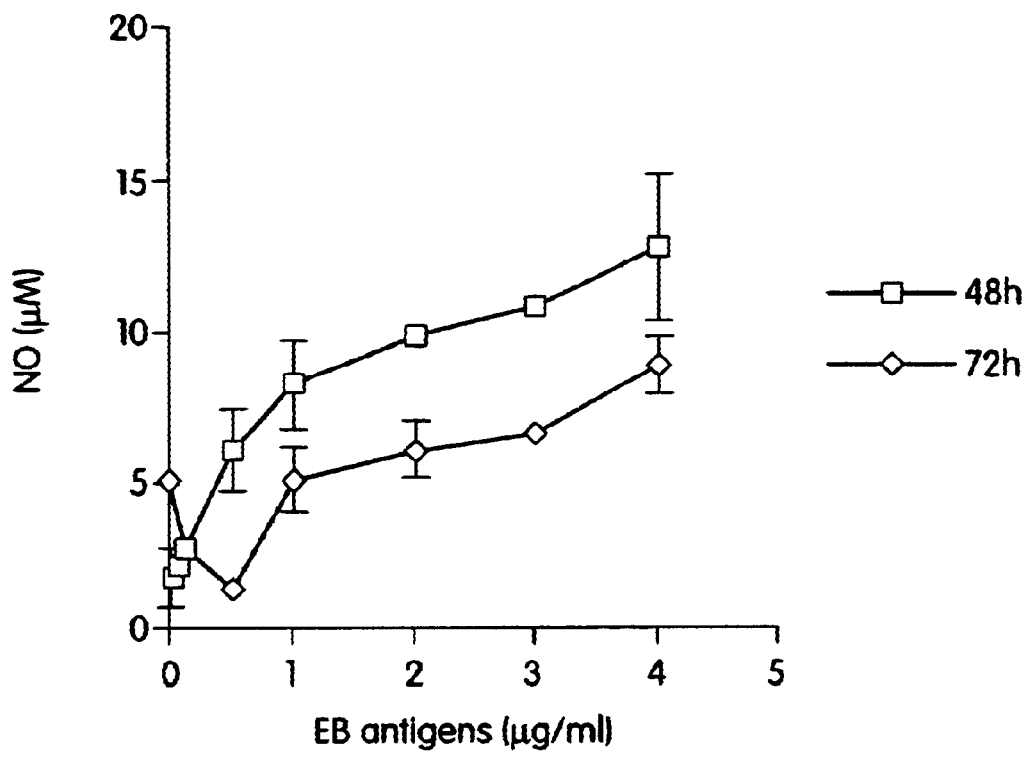
FIGS. 8A and 8B are schematic illustrations showing dose kinetics for induction of iNOS (expressed as NO levels in supernatants) in murine macrophage cultures following exposure to either EB antigens (FIG. 8A) or purified recombinant major outer membrane protein (MOMP) (FIG. 8B).
Figure 8B:
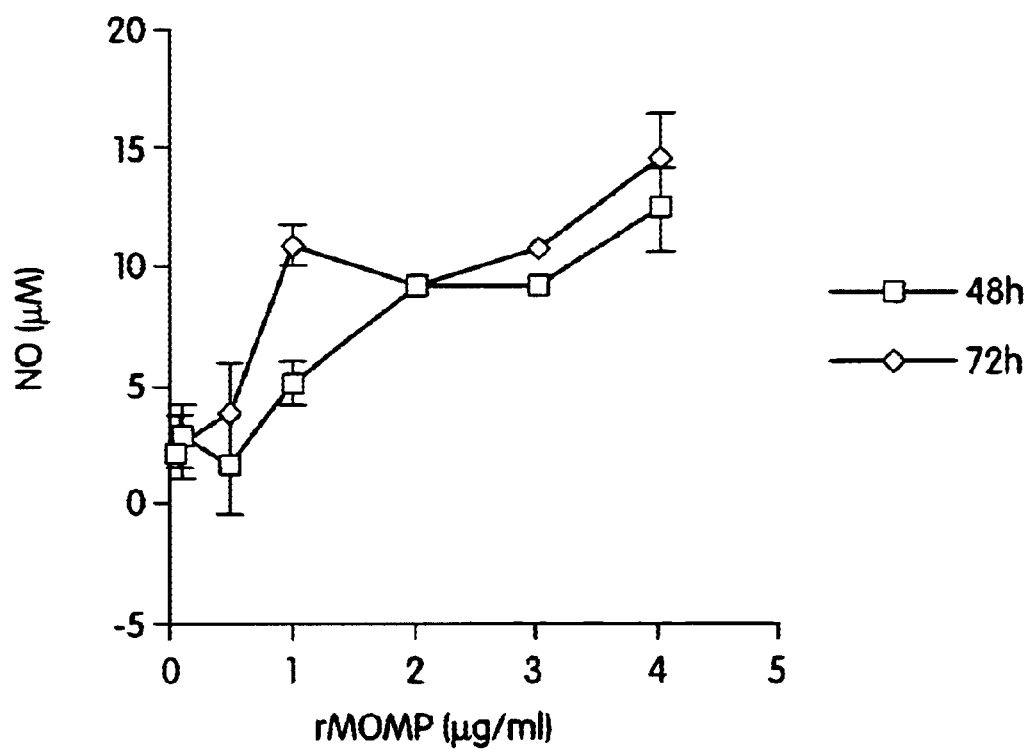

Induction of iNOS in Mouse Macrophages Exposed to *C. pneumoniae* EB Antigens and Purified rMOMP We examined the dose effect and kinetics of induction of nitrite in splenic macrophage cell culture supernatants following exposure to either EB antigens or purified rMOMP. As shown in FIGS. 8A and 8B, EB antigens of *C. pneumoniae* and rMOMP are each potent inducers of iNOS. Following addition of 4 µg/ml of EB antigens to macrophage cultures, nitrite levels in culture supernatants increased from 1.77±1 µM to 12.7±2.4 µM. When 4 µg/ml of rMOMP was added to macrophage cultures, nitrite levels increased from 2.4±0.4 µM to 14.5±1.8 µM. Endotoxin activity, as ascertained by limulus assay, was absent in either the EB antigen preparations or purified rMOMP, thereby excluding a possible contamination by LPS in these chlamydial antigen preparations as the reason for the induction of iNOS.

Figure 9:
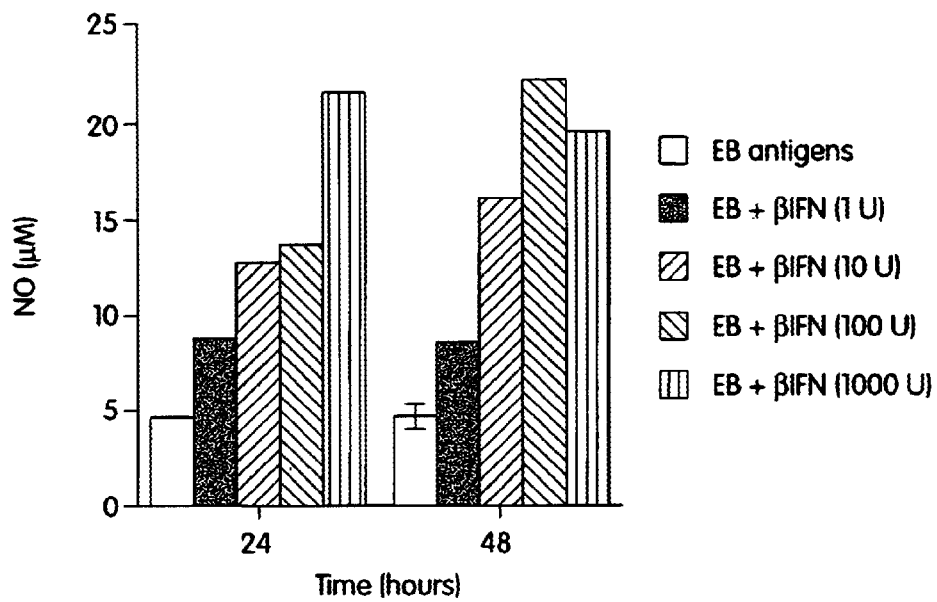
FIG. 9 is a schematic illustration showing enhancement of NO levels in macrophage cultures exposed to EB antigen (2 μg/ml) following pre-incubation with murine β-IFN.

Increase in iNOS Activity in Cells Pre-Treated With β-IFN and Cultured With EB Antigens and Purified rMOMP Addition of β-IFN to cultures prior to the addition of either EB antigens or purified rMOMP increased iNOS activity over that induced by the addition of either antigen alone (FIG. 9). At 48 hours, nitrite levels in supernatants increased from 5.1 µM in EB antigen-treated cultures to 19.6 µM after prior addition of 1000 U of β-IFN (FIG. 9). Addition of β-IFN alone did not increase nitrite levels in macrophage culture supernatants.

Figure 10:
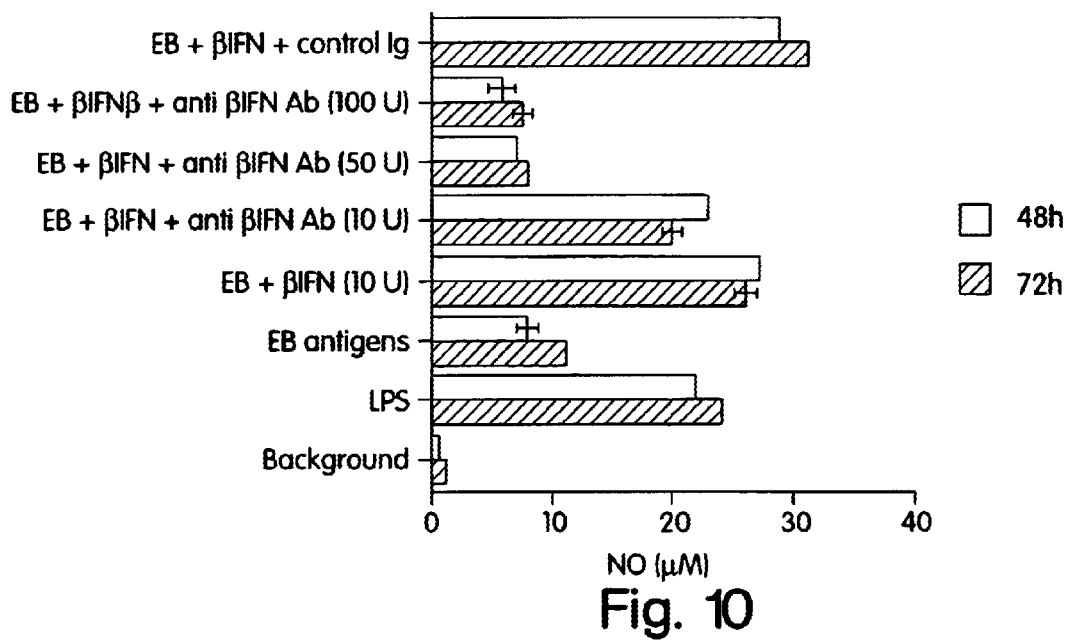
FIG. 10 is a schematic illustration showing that increases in NO levels are mediated by β-IFN. β-IFN was inactivated with specific sheep anti-mouse β-IFN antibody in amounts sufficient to neutralize 10 U of β-IFN. The amount of control sheep immunoglobulin added equaled Ig concentrations present in anti-sheep antibody that had the capacity to neutralize 100 U of β-IFN.
Figure 11A:
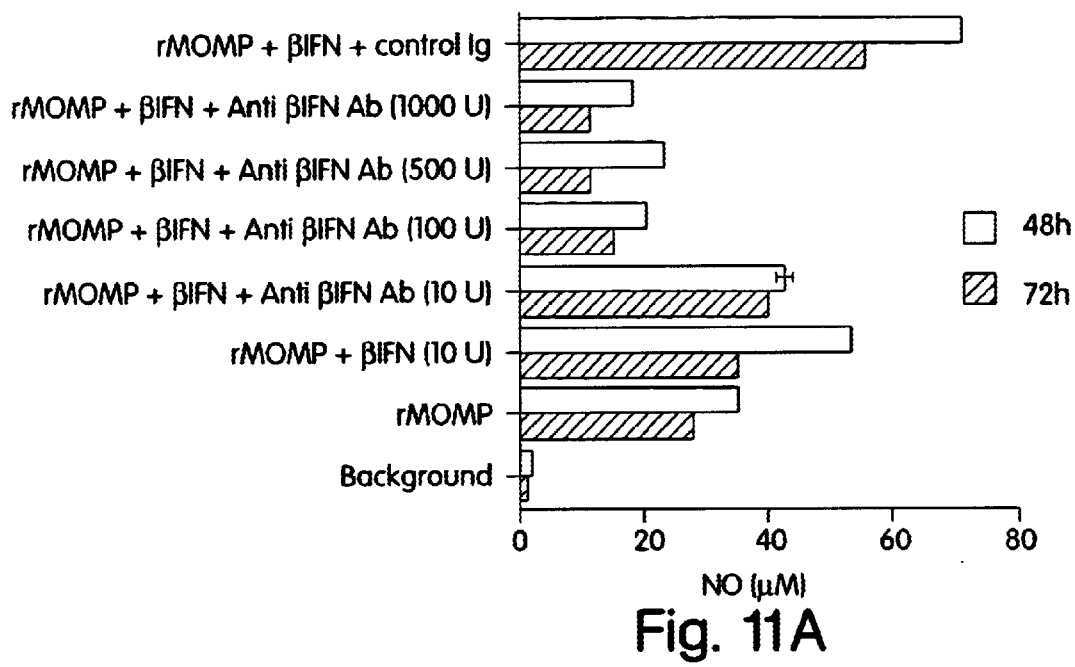
FIGS. 11A and 11B are schematic illustrations showing that enhancement of NO levels in macrophage cultures exposed to purified rMOMP (FIG. 11A) or LPS (FIG. 11B) is also mediated by β-IFN.
Figure 11B:
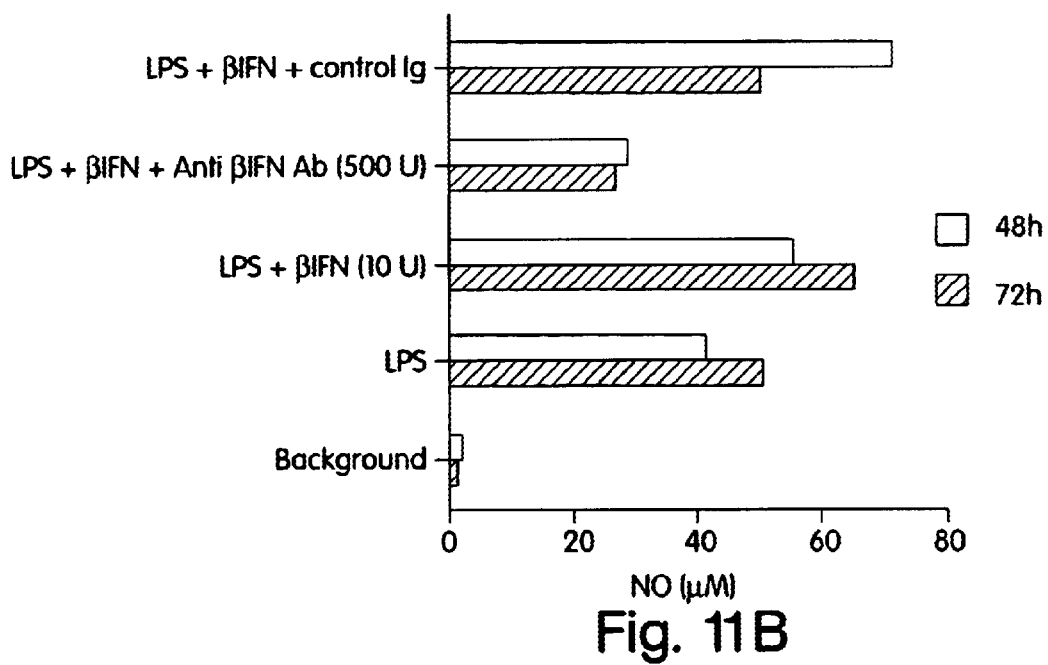

To further establish that the increase in NO activity was directly related to the addition of β-IFN, increasing concentrations of anti-β-IFN antibody was incubated with β-IFN. Sheep anti-mouse β-IFN antibody was added to neutralize the function of β-IFN. Sheep immunoglobulin that was added in amounts equal to that used to neutralize β-IFN was used as controls. The antigen-antibody complex was centrifuged at 13,000×g for 30 minutes, and unbound β-IFN was removed from the supernatant and added to macrophages cultures along with EB antigens. As shown in FIG. 10, the addition of 10 U of β-IFN increased nitrite levels in EB antigen-treated macrophages from 8.0±0.9 µM to 27.3±0.4 µM (measured at 48 hours). Incubation of β-IFN with anti-β-IFN antibody (an amount sufficient to neutralize 100 U of βIFN) reduced the amount of nitrite in the culture supernatants to basal levels. Incubation of βIFN with control sheep immunoglobulin did not inhibit nitrite levels, thus demonstrating the specificity of the β-IFN enhancing effect. Similar results were also obtained with addition of β-IFN to macrophage cell cultures prior to the addition of either rMOMP or LPS (FIGS. 11A and 11B). Addition of 10 U of β-IFN to macrophage cultures incubated with 2 µg/ml of rMOMP resulted in a 47% increase in the nitrite level of activity. Culture of macrophages with LPS to which 10 U of β-IFN was added increased NO by 35%. Pre-incubation of anti-β-IFN antibody abrogated the enhancement seen following addition of β-IFN following culture with either rMOMP or LPS.

Figure 12A:
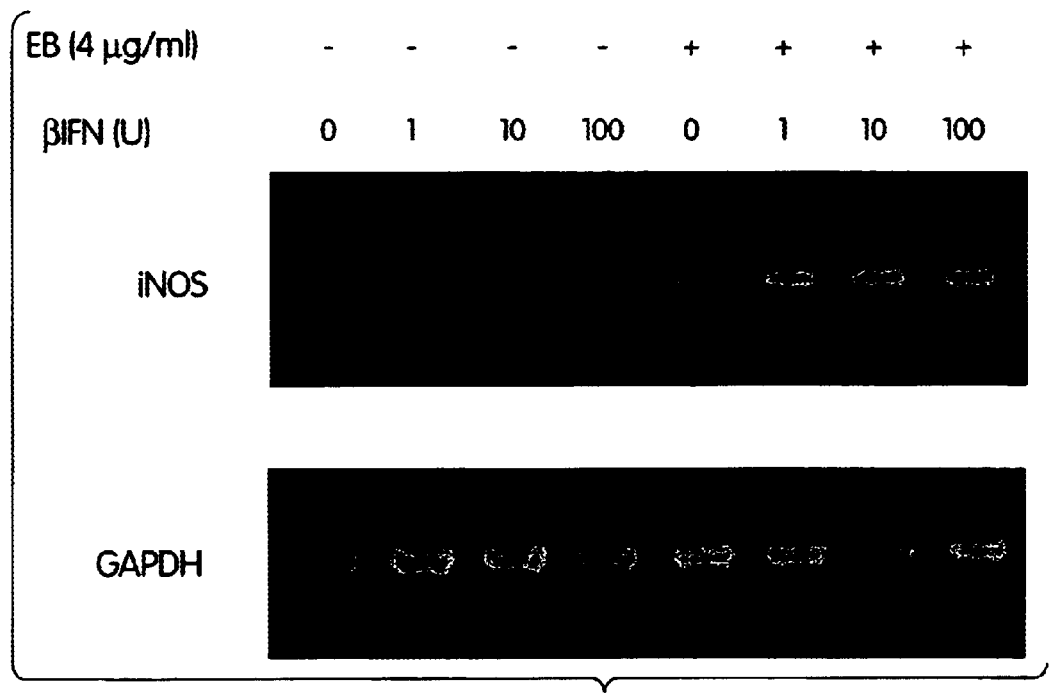
FIGS. 12A and 12B are schematic illustrations showing the results of an RT-PCR assay for the presence of iNOS2 gene products in murine macrophage cultures after exposure to EB antigens and purified rMOMP.
Figure 12B:
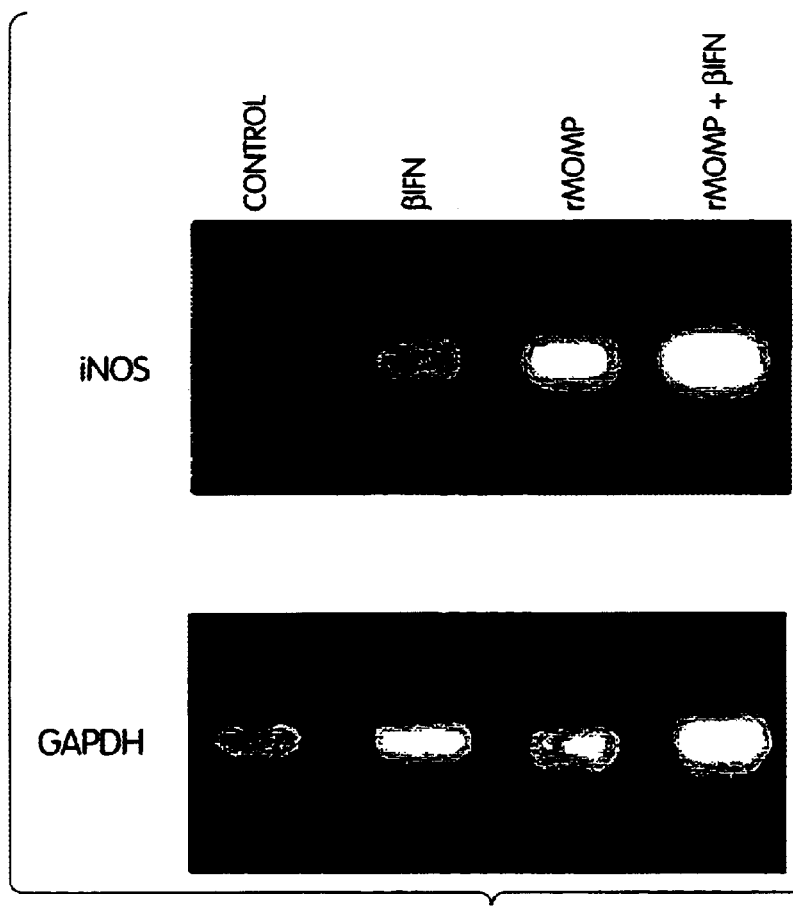

Effect of Addition of EB Antigens and Purified rMOMP to Macrophages on iNOS Induction We next determined if the increase in nitrite activity seen following addition of EB antigens or purified rMOMP was related to an increase in the induction of iNOS (NOS2) gene transcription. Although three NOS genes are present in mammalian cells, only NOS2 is inducible. Macrophages were treated with increasing amounts of murine β-IFN in the presence of either EB antigens or purified rMOMP. RT-PCR was performed using NOS primers, and the strength of the PCR signal was compared with the constitutively expressed mRNA for GAPDH. As shown in FIG. 12A, addition of β-IFN alone increased RT-PCR signals for NOS2 gene. Following addition of EB antigens (FIG. 12A) or purified rMOMP (FIG. 12B), however, a further amplification of the signal was noted. These results strongly suggests that both purified rMOMP and EB antigens of *C. pneumoniae* are capable of inducing iNOS, and this induction is enhanced following pre-incubation with β-IFN.

Effect of EB Antigens and Purified rMOMP on IL-12/p40 Production

We next examined the effect of EB antigens and purified rMOMP on the induction of IL-12/p40 in splenic macrophages. As shown in FIGS. 13A and 13B, a dose dependent increase in IL-12/p40 is seen following incubation with either EB antigens or purified rMOMP. Following addition of either EB antigens or purified rMOMP, a greater than 10-fold increase in IL-12/p40 was seen. Subsequent studies were done using 2 µg/ml of antigen.

Effect of β-IFN on IL-12/p40 Production

Macrophages were pretreated with β-IFN with IL-12/p40 levels in macrophage culture supernatants examined following addition of EB antigens of *C. pneumoniae*. As shown in FIG. 14, IL-12/p40 levels decreased from 6.6±0.2 ng/ml in EB antigen-treated cultures to 1.5±0.09 in cultures treated with EB antigens for 48 hours. Following the addition of 10 U of β-IFN, the induction of IL12/p40 is suppressed by 78%. To show specificity, anti-β-IFN antibody was added to the cultures, and its effect on IL-12/p40 was examined in a manner similar to that shown earlier. Addition of 500 U of anti-βIFN antibody abrogated the inhibitory effects of β-IFN on the induction of IL12/p40 by either EB antigens (100% reduction; FIG. 15A) or by rMOMP (54% reduction; FIG. 15B). Addition of equal amounts of control sheep immunoglobulin did not affect the inhibitory effects of β-IFN.

EXAMPLE 5

Treatment of MS by Administering Anti-Chiamydial Agents

Table 8 shows the course of therapy for a number of MS patients treated with a combination of anti-chlamydial agent. The case histories for these patients are described in Table 9. Table 10 lists the standard dosages for the drugs listed in Table 8.

TABLE 8

| Patient | Sex | Treatment Regimen | Duration (months) | Comments |
|---|---|---|---|---|
| BL | M | Rifampin Metronidazole Ofloxacin | 2 | |

TABLE 8-continued

| Patient | Sex | Treatment Regimen | Duration (months) | Comments |
|---|---|---|---|---|
| | | Metronidazole Sulfamethoxazole/ Trimethoprim Levaquin | 5 | |
| | | | 3 | Discontinued therapy, had relapse |
| | | Metronidazole Sulfamethoxazole/ Trimethoprim Levaquin | 2 | |
| | | Metronidazole Sulfamethoxazole/ Trimethoprim Levaquin Penicillamine | 7 | |
| | | Rifampin INH Penicillamine Probenecid | 3 | |
| MC | M | Rifampin INH Metronidazole | 9 | |
| | | Levaquin Minocycline | 6 | Probably not compliant |
| | | — | — | Discontinued |
| JM | M | Metronidazole Ofloxacin Sulfamethoxazole/ Trimethoprim Minocycline | 7 | |
| | | Amoxicillin Levaquin Sulfamethoxazole/ Trimethoprim | 4 | |
| | | Amoxicillin Levaquin Sulfamethoxazole/ Trimethoprim Probenecid | 3 | |
| LL | F | Metronidazole Levaquin Minocycline | 15 | |
| | | Penicillamine Levaquin Minocycline Probenecid | 1 | |
| FO | M | Prednizone | 0.25 | Phased in over several days to mitigate effect of therapy |
| | | Metronidazole Clarithromycin | 2 | |
| | | Clarithromycin | 1 | Stopped metronidazole due to persistence of side effects |
| | | Clarithromycin Kemet | 0.5 | |
| | | Metronidazole Clarithromycin Kemet | 6 | Began phasing metronidazole back in over a month |
| | | Metronidazole Clarithromycin Kemet Amoxicillin | 1 | Began two week switchover to Amoxicillin |
| | | Metronidazole Clarithromycin Amoxicillin | 2 | |
| | | Metronidazole Clarithromycin Amoxicillin Probenecid | 6 | |
| JC | F | Amoxicillin | 1 | |
| | | Amoxicillin Probenecid | 1 | |
| | | Amoxicillin Probenecid Sulfamethoxazole/ Trimethoprim | 1 | |
| | | Amoxicillin Probenecid Sulfamethoxazole/ Trimethoprim INH | 7 | |
| FW | M | Penicillamine Metronidazole Doxycycline | 7 | |
| | | Penicillamine INH Sulfamethoxazole/ Trimethoprim Probenecid | 5 | |
| | | — | — | |

TABLE 9

| Patient | Case History |
|---|---|
| BL | First symptoms began with numbness of the left arm and leg which rapidly progressed to a partial Brown-Sequard syndrome (i.e. cord myelitis) with an associated urinary retention. Despite therapy with corticosteroids, and β-IFN, he rapidly progressed over the next three months with an EDSS = 8.0 (triplegic plus speech and swallowing impairments). A positive CSF PCR and culture for *C. pneumoniae* led to treatment with combination antibiotics. The patient improved in all aspects of neurologic function over the following six months. His EDSS score nine months later was 3.0 with return to work and routine athletic activities. His neurological status remains stable and he continues on an anti-chlamydial combination regimen. |
| MC | This patient had a ten year history of MS with evidence of progressive ataxia and weakness in the legs. Over five months his EDSS score worsened from a 7.0 to 8.0. His CFS was positive by PCR for *C. pneumoniae* and he was placed on combination antibiotics. Over the next six months he gradually improved in his balance, coordination and lower extremity strength. His most recent EDSS score was 6.5. |
| JM | Initially seen with rapidly progressive paraparesis secondary to MS. He failed to response to corticosteroids on two successive occasions. Five months later, his EDSS score was 7.5. Following a positive *C. pneumoniae* PCR, he was placed on combination antibiotics. He has gradually gain strength in his lower extremities and five months later was able to walk with a walker (EDSS = 6.5) while maintaining on combination antibiotics. |

TABLE 9-continued

| Patient | Case History |
|---|---|
| LL | Patient with a long history (14 years) of secondary progressive MS with recent progressive bulbar symptoms, axtaxia, and paraplegia (EDSS = 8.5). PCR for the MOMP gene of *C. pneumoniae* in the CSF was positive. She was placed on combination antibiotics with no further progression of symptoms for the last six months. |
| AN | Long history of MS and wheel chair bound for approximately ten years. She has received continuous physical therapy to retain leg muscle tone. Following approximately six months of combination antibiotics, she was able to stand unaided and take several unaided steps. She reports significant decrease in fatigue and cognitive dysfunction. She remains on combination antibiotics and other supportive medications. |
| FO | Wheel chair bound with a long history of MS with a two–three year progression of severe dysarthriae and incontinence. On combination antibiotics (14 months) he has had improvement of speech and incontinence. Speech, ability to open mouth for dentist, stamina all improved. He can stand better on his own mid-transfer, but remains wheelchair-bound. |
| JC | Diagnosis of MS with development of a foot drop approximately one year prior to therapy requiring the use of a cane in walking. Approximately four months after initiation of combination antibiotic therapy, patient reports reversal of foot drop and no longer requires a cane. She continues on antibiotic therapy. |
| FW | Male with a 15 year history of MS. Used a cane for a rolling, unstable gait. Easily fatigued. After 12 months of combination antibiotics, was able to walk without cane or excessive fatigue, although his gait can still wander. Can easily make it across the parking lot, which had previously been a challenge. Stopped antibiotics even though was still PCR positive; plans to restart therapy if he has another flare-up. |

TABLE 10

| Drug | Generic | Unit dosage | Daily dosage |
|---|---|---|---|
| Cupramine | Penicillamine | 250 mg | 2X |
| Amoxicillin | | 500 mg | 2X |
| Flagyl | Metronidazole | 500 mg | 2X |
| INH | | 300 mg | 1X |
| Rifampin | | 300 mg | 2X |
| Floxin | Ofloxacin | 400 mg | 2X |
| Levaquin | | 500 mg | 1X |
| Bactrim | SMZ/TMP | Double Strength | 2X |
| Biaxin | Clarythromycin | 500 mg | 2X |
| Minocycline | | 100 mg | 2X |
| Doxycycline | | 100 mg | 2X |
| Probenecid | | 500 mg | 2X |

The efficacy of long-term administration of combination therapy in the treatment of 11 patients with secondary progressive MS and one patient with primary progressive MS (patient #6) is shown in Table 11. All 12 patients were positive by PCR for the MOMP gene of *C. pneumoniae* in the CSF. In 10 of 12 patients, the highest Expanded Disability Status Scale (EDSS; Kurtzke, Neurology 33:1444–1152, 1983) score reached was sustained for six months. In patient #1, the maximal EDSS was present for four months and improved when he was treated with antibiotics for urosepsis. The antibiotic regimen in eight of 12 patients was a combination of rifampin (300 mg twice daily), amoxicillin (500 mg twice daily) and probenecid (500 mg daily). Patient #5 discontinued use of amoxicillin after three months and was continued on rifampin alone. Patients #3 and #10 were administered rifampin and levofloxacin. In patient #12, azithromycin was substituted for rifampin in view of the gastrointestinal side effects. Patients #1, #10, #11, and #12 also received β-IFN.

Overall, six patients improved by the EDSS and, in each case, improvement has been maintained for at least six months. Of the six patients who showed no changes on the EDSS, patient #2 had sustained improvement in upper extremity function as measured by the nine hole peg test. In patient #4, the EDSS did not change, but her ambulation index (time to walk 25 feet) improved from 52.8 seconds at the time of institution of antibiotics to 32.5 seconds at time of completion. In patient #8, there was a sustained improvement in his visual acuity. Patient #10 had an increase in her EDSS from 6.0 to 8.0 while on rifampin and levofloxacin.

TABLE 11

| Patient | Age/Sex | EDSS | Duration | Antibiotics | Steroids | Other Drugs | Duration of Antibiotics | EDSS II | Improved | PCR Signal Post-antibiotics |
|---|---|---|---|---|---|---|---|---|---|---|
| 1 | 34/M | 7.5 | 3 m | Rifampin Amoxicillin | No | β-IFN1b | 12 m | 6.5 | Yes | Absent |
| 2 | 36/F | 8.5 | 6 m | Rifampin Amoxicillin | No | No | 12 m | 8.5 | Yes | Decreased |
| 3 | 49/F | 8.5 | 9 m | Rifampin Levoflaxacin | No | No | 15 m | 8.0 | Yes | No change |
| 4 | 41/F | 6.5 | 18 m | Rifampin Amoxicillin | No | No | 9 m | 6.5 | Yes | ND |
| 5 | 54/M | 8.0 | 9 m | Rifampin | No | No | 10 m | 7.5 | Yes | ND |
| 6 | 33/F | 8.5 | 5 m | Rifampin Amoxicillin | Yes | No | 12 m | 8.0 | Yes | Absent |
| 7 | 57/M | 8.5 | 24 m | Rifampin Amoxicillin | No | No | 12 m | 8.5 | No | ND |
| 8 | 34/M | 3.0 | 8 m | Rifampin Amoxicillin | Yes | Cop-1 | 12 m | 2.5 | Yes | ND |
| 9 | 38/F | 6.5 | 6 m | Rifampin Amoxicillin | No | No | 9 m | 5.5 | Yes | Decrease |

TABLE 11-continued

| Patient | Age/Sex | EDSS | Duration | Antibiotics | Steroids | Other Drugs | Duration of Antibiotics | EDSS II | Improved | PCR Signal Post-antibiotics |
|---------|---------|------|----------|-------------|----------|-------------|-------------------------|---------|----------|------------------------------|
| 10 | 25/F | 6.0 | 3 m | Rifampin Levoflaxacin | Yes | β-IFN | 12 m | 8.0 | No | ND |
| 11 | 26/F | 6.0 | 6 m | Rifampin Amoxicillin | No | β1a | 6 m | 3.0 | Yes | ND |
| 12 | 42/F | 6.0 | 6 m | Azithromycin | Yes | β-IFN1a | 9 m | 6.0 | No | Absent |

EXAMPLE 6

Animal Models for the Identification of Drugs for the Treatment of MS

The discovery that chlamydial infection correlates with MS allows for the development of animal models for drug identification. For example, an animal (e.g., a mouse, rat, or rabbit) can be infected by injecting Chlamydia into the ventricles of the brain. Once infection of the brain has been established, candidate compounds can be administered to the animal using any mode of administration described above for the administration of compounds to humans. The ability of the compound to eradicate the infection can be ascertained by performing one or more of the assays described herein. For example, the detection of chlamydial DNA (e.g., the MOMP gene or the 16S RNA gene) in the CSF or blood of the animals can be performed using the methods described in Examples 1 and 2. If desired, the animal can be sacrificed and the tissue examined using standard histological methods for the detection of chlamydial infection.

Alternatively, MS therapeutics may be identified using any other method for identifying anti-chlamydial agents. A number of such screening assays are described in co-pending U.S. patent application Ser. No. 09/073,661.

Other Embodiments

All patent applications and publications mentioned in this specification are herein incorporated by reference to the same extent as if each independent patent application and publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth.

Other embodiments are within the claims.

What is claimed is:

1. A method of treating an individual diagnosed to have multiple sclerosis, comprising administering to the individual an effective amount of at least one anti-chlamydial agent and an agent that increases iNOS activity, wherein the individual is administered both agents until the individual tests negative for elementary body phase Chlamydia, replicating phase Chlamydia, and cryptic phase Chlamydia.

2. The method of claim 1, wherein the agent that increases iNOS activity is a type-1 interferon, a synthetic type-1 interferon analog, or a hybrid type-1 interferon, wherein the type-1 interferon analog or hybrid binds to the same receptor as a naturally-occurring type-1 interferon.

3. The method of claim 2, wherein the type-1 interferon is β-interferon.

4. The method of claim 1, wherein the individual is administered at least two anti-chlamydial agents.

5. The method of claim 4, wherein the anti-chlamydial agents are selected from the group consisting of rifamycins, azalides, ketolides, streptogramins, ampicillin, amoxicillin, quilolones, fluoroquinolones, sulfonamides, isonicotinic congeners, and tetracyclines.

6. A method of treating an individual diagnosed to have multiple sclerosis, comprising administering to the individual an effective amount of at least one anti-chlamydial agent selected from the group consisting of rifamycins, azalides, ketolides, streptogramins, ampicillin, amoxicillin, quilolones, fluoroquinolones, sulfonamides, isonicotinic congeners, and tetracyclines.

7. The method of claim 6, wherein the individual is administered the anti-chlamydial agent until the individual tests negative for elementary body phase Chlamydia, replicating phase Chlamydia, and cryptic phase Chlamydia.

8. The method of claim 6, wherein the individual is administered the anti-chlamydial agent for at least 45 days.

9. The method of claim 8, wherein the individual is administered the anti-chlamydial agent for at least 90 days.

10. The method of claim 9, wherein the individual is administered the anti-chlamydial agent for at least 180 days.

11. The method of claim 6, wherein the individual is also administered an effective amount of an agent that increases iNOS activity.

12. The method of claim 11, wherein the agent that increases iNOS activity is a type-1 interferon, a synthetic type-1 interferon analog, or a hybrid type-1 interferon, wherein the type-1 interferon analog or hybrid binds to the same receptor as a naturally-occurring type-1 interferon.

13. The method of claim 12, wherein the type-1 interferon is β-interferon.

14. The method of claim 6, wherein said anti-chlamydial agent is a rifamycin.

15. A method of treating an individual diagnosed to have multiple sclerosis, comprising administering to the individual an effective amount of at least one anti-chlamydial agent and an agent that increases iNOS activity.

16. The method of claim 15, wherein the agent that increases iNOS activity is a type-1 interferon, a synthetic type-1 interferon analog, or a hybrid type-1 interferon, wherein the type-1 interferon analog or hybrid binds to the same receptor as a naturally-occurring type-1 interferon.

17. The method of claim 16, wherein the type-1 interferon is β-interferon.

18. The method of claim 15, wherein said anti-chlamydial agent is a rifamycin.

* * * * *

UNITED STATES PATENT AND TRADEMARK OFFICE
CERTIFICATE OF CORRECTION

PATENT NO.    : 6,710,033 B1
DATED         : March 23, 2004
INVENTOR(S)   : Stratton et al.

It is certified that error appears in the above-identified patent and that said Letters Patent is hereby corrected as shown below:

Column 2,
Line 54, "receptable" should be -- receptacle --.

Column 3,
Line 5, "adminstration" should be -- administration --.
Line 64, "quilolones" should be -- quinolones --.

Column 4,
Line 4, "Chiamydia" should be -- Chlamydia --.

Column 5,
Line 34, "quilolones" should be -- quinolones --.
Line 42, "drugs for the such treatment" should be -- drugs for such treatment --.

Column 10,
Line 51, "have" should be -- has --.

Column 11,
Lines 27 and 49, "persistance" should be -- persistence --.
Line 64, "chiamydial" should be -- chlamydial --

Column 14,
Line 64, "arnithine" should be -- ornithine --.

Column 24,
Line 22, "centrifuiged" should be -- centrifuged --.

Column 26,
Line 67, "were" should be -- was --.

Column 27,
Line 8, "microcentriflige" should be -- microcentrifuge --.

Column 30,
Line 50, "were" should be -- was --.

Column 33,
Line 32, "fluoroscein" should be -- fluorescein --.

UNITED STATES PATENT AND TRADEMARK OFFICE
CERTIFICATE OF CORRECTION

PATENT NO. : 6,710,033 B1
DATED : March 23, 2004
INVENTOR(S) : Stratton et al.

It is certified that error appears in the above-identified patent and that said Letters Patent is hereby corrected as shown below:

Column 36,
Line 19, "suggests" should be -- suggest --.
Line 52, "Chiamydia" should be -- Chlamydia --.

Column 46,
Lines 59 and 66, "quilolones" should be -- quinolones --.

Signed and Sealed this

Thirteenth Day of July, 2004

JON W. DUDAS
*Acting Director of the United States Patent and Trademark Office*

SEQUENCE LISTING

<160> NUMBER OF SEQ ID NOS: 14

<210> SEQ ID NO 1
<211> LENGTH: 38
<212> TYPE: DNA
<213> ORGANISM: Artificial Sequence
<220> FEATURE:
<223> OTHER INFORMATION: Based on Chlamydia pneumoniae
<400> SEQUENCE: 1
atgaaaaaac tcttaaagtc ggcgttatta tccgccgc                38

<210> SEQ ID NO 2
<211> LENGTH: 40
<212> TYPE: DNA
<213> ORGANISM: Artificial Sequence
<220> FEATURE:
<223> OTHER INFORMATION: Based on Chlamydia pneumoniae

<400> SEQUENCE: 2
ttagaatctg aactgaccag atacgtgagc agctctctcg                40

<210> SEQ ID NO 3
<211> LENGTH: 24
<212> TYPE: DNA
<213> ORGANISM: Artificial Sequence
<220> FEATURE:
<223> OTHER INFORMATION: Based on Chlamydia pneumoniae

```
<400> SEQUENCE: 3
gctgctgcaa actatactac tgcc                                              24

<210> SEQ ID NO 4
<211> LENGTH: 25
<212> TYPE: DNA
<213> ORGANISM: Artificial Sequence
<220> FEATURE:
<223> OTHER INFORMATION: Based on Chlamydia pneumoniae

<400> SEQUENCE: 4
gaatcagtag tagacaatgc tgtgg                                             25

<210> SEQ ID NO 5
<211> LENGTH: 22
<212> TYPE: DNA
<213> ORGANISM: Artificial Sequence
<220> FEATURE:
<223> OTHER INFORMATION: Based on Chlamydia pneumoniae

<400> SEQUENCE: 5
tttagtggcg gaagggttag ta                                                22

<210> SEQ ID NO 6
<211> LENGTH: 22
<212> TYPE: DNA
<213> ORGANISM: Artificial Sequence
<220> FEATURE:
<223> OTHER INFORMATION: Based on Chlamydia pneumoniae

<400> SEQUENCE: 6
cacatatcta cgcatttcac cg                                                22

<210> SEQ ID NO 7
<211> LENGTH: 25
<212> TYPE: DNA
<213> ORGANISM: Artificial Sequence
<220> FEATURE:
<223> OTHER INFORMATION: Based on Chlamydia pneumoniae

<400> SEQUENCE: 7
ctttcggttg aggaagagtt tatgc                                             25

<210> SEQ ID NO 8
<211> LENGTH: 29
<212> TYPE: DNA
<213> ORGANISM: Artificial Sequence
<220> FEATURE:
<223> OTHER INFORMATION: Based on Chlamydia pneumoniae

<400> SEQUENCE: 8
tcctctagaa agatagtttt aaatgctga                                         29

<210> SEQ ID NO 9
<211> LENGTH: 39
<212> TYPE: DNA
<213> ORGANISM: Artificial Sequence
<220> FEATURE:
<223> OTHER INFORMATION: Based on Chlamydia pneumoniae

<400> SEQUENCE: 9
agcttaccat ggtgaatgaa aaaactctta aagtcggcg                              39
```

```
<210> SEQ ID NO 10
<211> LENGTH: 40
<212> TYPE: DNA
<213> ORGANISM: Artificial Sequence
<220> FEATURE:
<223> OTHER INFORMATION: Based on Chlamydia pneumoniae

<400> SEQUENCE: 10
atatgcggcc gctcattaga atctgaactg accagatacg                    40

<210> SEQ ID NO 11
<211> LENGTH: 20
<212> TYPE: DNA
<213> ORGANISM: Artificial Sequence
<220> FEATURE:
<223> OTHER INFORMATION: Based on Chlamydia pneumoniae

<400> SEQUENCE: 11
tagaggaaca tctggccagg                                          20

<210> SEQ ID NO 12
<211> LENGTH: 20
<212> TYPE: DNA
<213> ORGANISM: Artificial Sequence
<220> FEATURE:
<223> OTHER INFORMATION: Based on Chlamydia pneumoniae

<400> SEQUENCE: 12
tggcagcatc ccctctgatg                                          20

<210> SEQ ID NO 13
<211> LENGTH: 26
<212> TYPE: DNA
<213> ORGANISM: Artificial Sequence
<220> FEATURE:
<223> OTHER INFORMATION: Based on Chlamydia pneumoniae

<400> SEQUENCE: 13
tgaaggtcgg tgtgaacgga tttggc                                   26

<210> SEQ ID NO 14
<211> LENGTH: 24
<212> TYPE: DNA
<213> ORGANISM: Artificial Sequence
<220> FEATURE:
<223> OTHER INFORMATION: Based on Chlamydia pneumoniae

<400> SEQUENCE: 14
catgtaggcc atgaggtcca ccac                                     24
```